(12) United States Patent
Smetak et al.

(10) Patent No.: US 7,289,227 B2
(45) Date of Patent: Oct. 30, 2007

(54) SYSTEM AND TRACKER FOR TRACKING AN OBJECT, AND RELATED METHODS

(75) Inventors: Edward Charles Smetak, Katy, TX (US); John David Scherch, Pittsburgh, PA (US)

(73) Assignee: Nomos Corporation, Cranberry Township, PA (US)

( * ) Notice: Subject to any disclaimer, the term of this patent is extended or adjusted under 35 U.S.C. 154(b) by 459 days.

(21) Appl. No.: 10/957,128

(22) Filed: Oct. 1, 2004

(65) Prior Publication Data

US 2006/0072124 A1 Apr. 6, 2006

(51) Int. Cl.
*G01B 11/26* (2006.01)

(52) U.S. Cl. ...................................... 356/614

(58) Field of Classification Search ............... None
See application file for complete search history.

(56) References Cited

U.S. PATENT DOCUMENTS

| | | | |
|---|---|---|---|
| 3,861,807 A | 1/1975 | Lescrenier et al. | |
| 3,987,281 A | 10/1976 | Hodes et al. | |
| 4,396,945 A | 8/1983 | DiMatteo et al. | |
| 4,455,609 A | 6/1984 | Inamura et al. | |
| 4,649,504 A | 3/1987 | Krouglicof et al. | |
| 5,197,476 A | 3/1993 | Nowacki et al. | |
| 5,227,985 A | 7/1993 | DeMenthon | |
| 5,373,844 A | 12/1994 | Smith et al. | |
| 5,511,549 A | 4/1996 | Legg et al. | |
| 5,828,770 A | 10/1998 | Leis et al. | |
| 6,288,785 B1 | 9/2001 | Frantz et al. | |
| 6,360,116 B1 | 3/2002 | Jackson et al. | |
| 6,435,717 B1 | 8/2002 | Koehler et al. | |
| 6,560,311 B1 | 5/2003 | Shepard et al. | |
| 6,876,459 B2 * | 4/2005 | Tu et al. ..................... | 356/614 |
| 6,909,515 B2 * | 6/2005 | Madsen et al. ............. | 356/614 |
| 6,980,303 B2 * | 12/2005 | Kume et al. ................ | 356/614 |
| 2002/0080915 A1 | 6/2002 | Frohlich et al. | |
| 2002/0122530 A1 | 9/2002 | Erbel et al. | |
| 2004/0138556 A1 | 7/2004 | Cosman | |

FOREIGN PATENT DOCUMENTS

| | | |
|---|---|---|
| EP | 0911065 A | 4/1999 |
| EP | 1041918 | 11/2000 |
| WO | WO 02/49044 A2 | 6/2002 |

OTHER PUBLICATIONS

Polaris Tool Design Guide, dated Apr. 2004; copyright 2004 Northern Digital Inc.

* cited by examiner

*Primary Examiner*—Tu T. Nguyen
(74) *Attorney, Agent, or Firm*—Bracewell & Giuliani LLP

(57) ABSTRACT

A system to track a three-dimensional position and an orientation of a movable object and associated methods are provided. The system includes a tracker having an optically trackable body adapted to connect to the movable object. A plurality of optical indicators are connected or mounted to the optically trackable body to form a plurality of geometric figures. A plurality of obfuscating flanges optically separate the optical indicators from each other to prevent each of the optical indicators from becoming optically coincident with another optical indicator when viewed along a preselected viewing path. The system also includes an apparatus to track the tracker having an optical detector to simultaneously detect the three-dimensional position of at least three of the plurality of optical indicators and a determiner to determine the three-dimensional position and orientation of the optically trackable body from the position of the optical indicators.

33 Claims, 9 Drawing Sheets

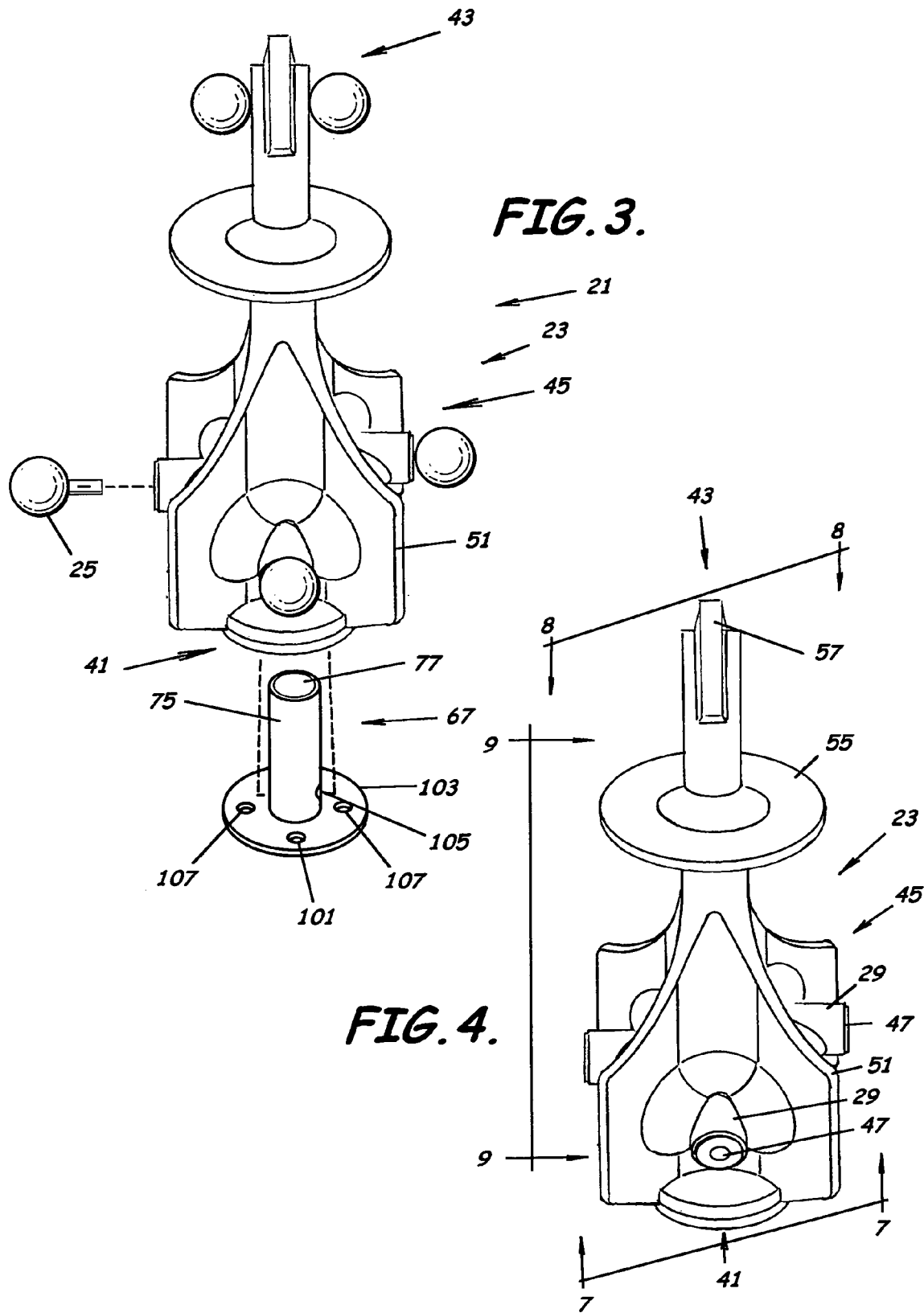

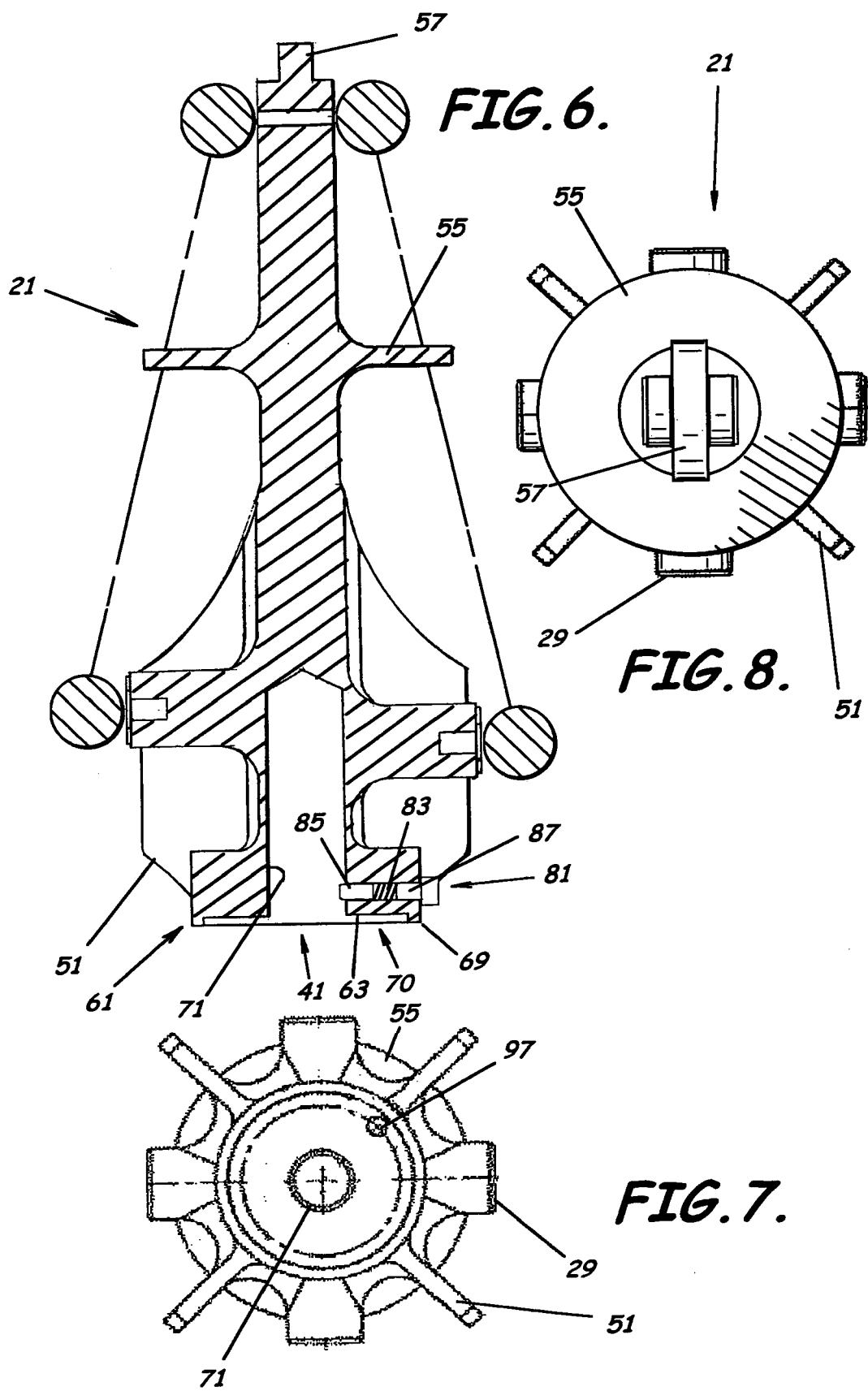

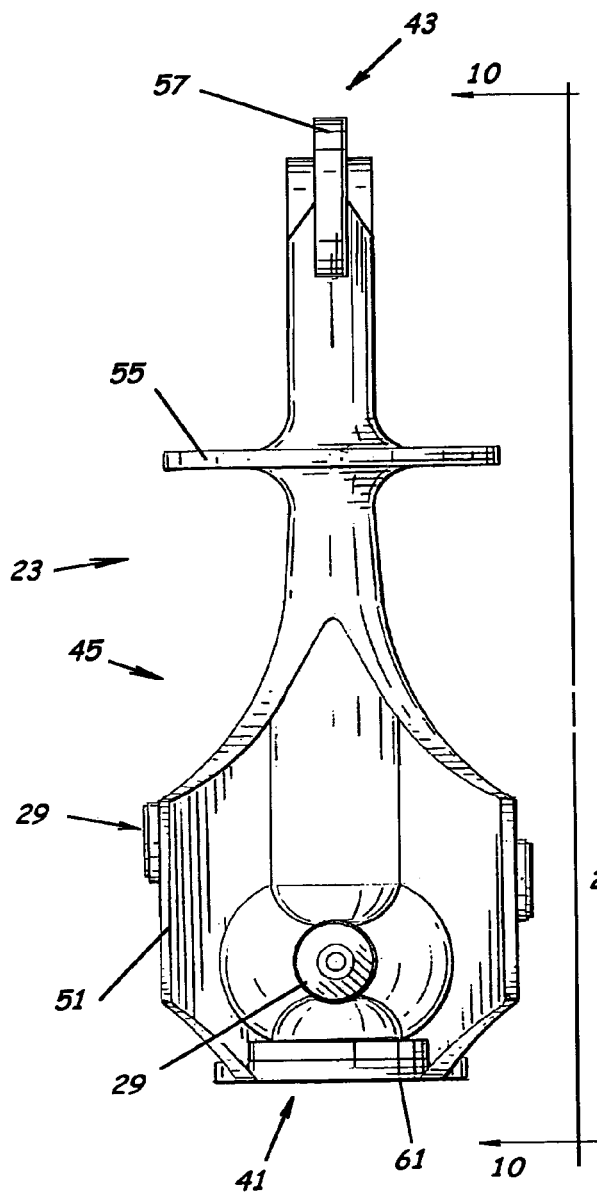
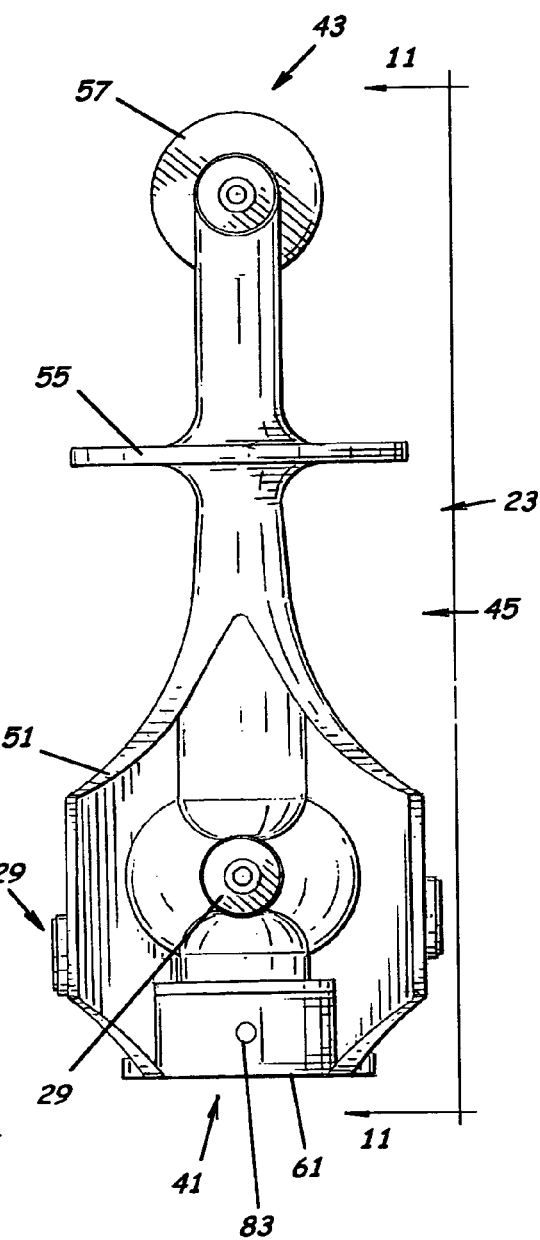

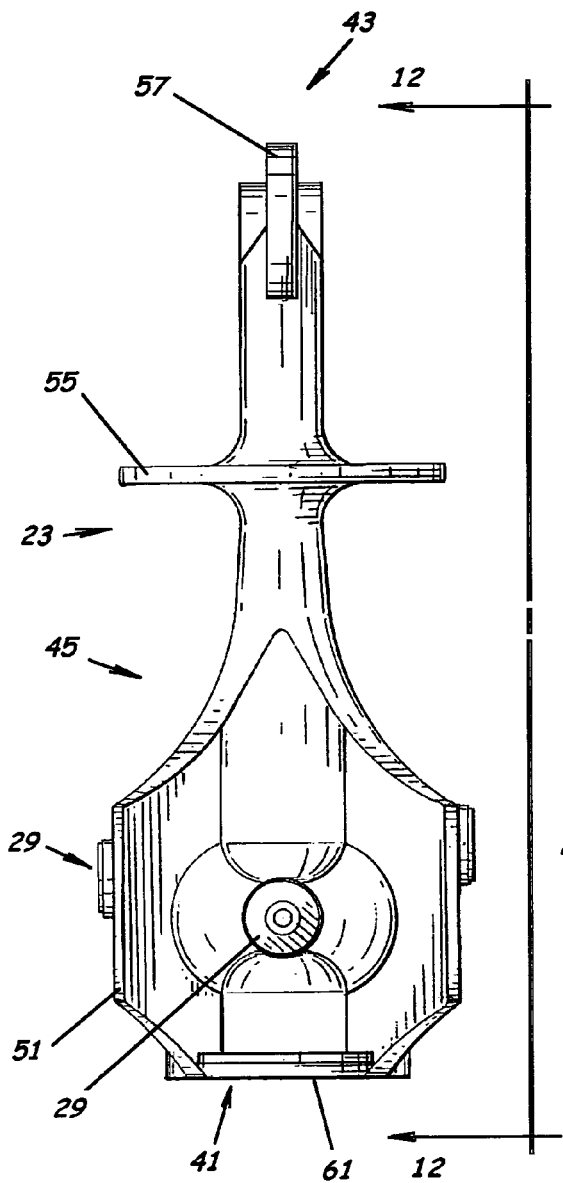
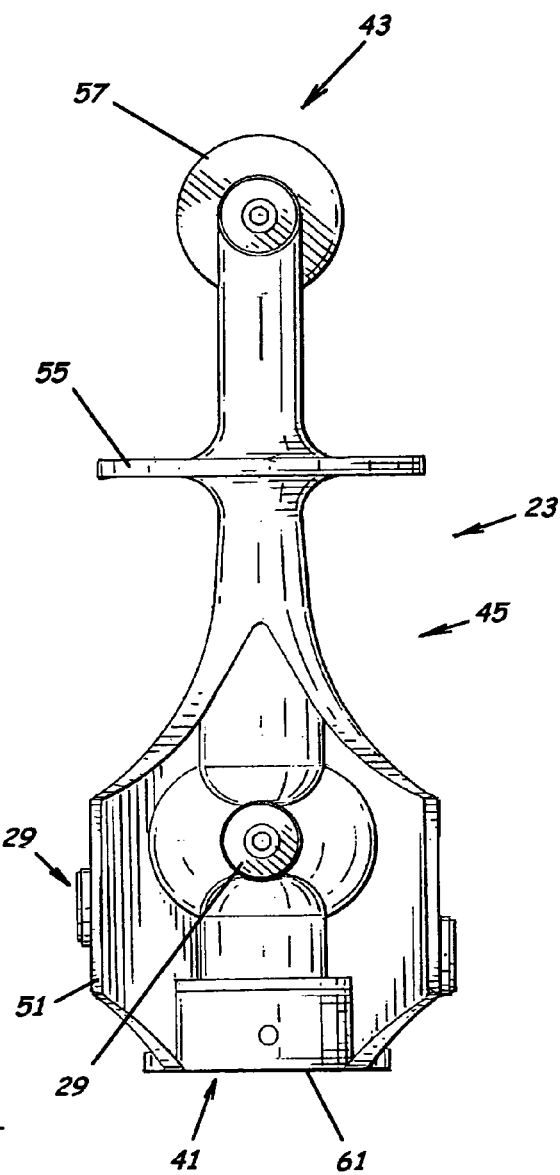

SYSTEM AND TRACKER FOR TRACKING AN OBJECT, AND RELATED METHODS

BACKGROUND OF THE INVENTION

1. Field of the Invention

The present invention relates to tracking apparatus. More specifically, the present invention relates to a system, a tracker, and related methods for tracking spatial position and orientation of an object.

2. Description of the Related Art

It is often desired to track the position and orientation of an object. For example, in the electronics industry it is often necessary to match surfaces or insert parts in predetermined positions. This is especially significant where a robot or robotic arm is used. In the medical field, it is often necessary to track the position of a medical instrument in order to determine the location of an object within a body. For example, knowledge of the position of a surgical tool during neurosurgery or location of a target such as a tumor while radiation therapy treatment is occurring, have always been critical issues.

Also, in the medical field, recent diagnostic advances such as computerized tomographic (CT) scans, magnetic resonance imaging (MRI) scanning, and positron emission tomographic (PET) scanning have greatly facilitated preoperative diagnosis and surgical or radiation planning. Precision and accuracy of the scanning technologies, however, have not been fully developed in order to utilize such diagnostic advances during treatment to their fullest potential. For example, with respect to radiation therapy, it is assumed that the patient's position and the target's position within the patient will be grossly, or nominally, the same at the time of radiation treatment, as it was at the time the radiation treatment plan was created. If the position of the target is not the same as it was at the time the treatment plan was determined, the dose of radiation may not be delivered to the correct location within the patient's body. Because patients are not always positioned properly on the treatment table of the radiation therapy device, which may be a linear accelerator or a cobalt unit, and because organs of a patient may move within the patient from day to day, the target may not be positioned at the exact location where the radiation therapy plan has assumed it would be located. Various systems and tools have been developed to determine the target position and orientation.

The position of an object or tool is typically defined by three translation parameters (x, y, z) and three rotation parameters (pitch, roll, yaw) corresponding to six degrees of freedom. The translation parameters (x, y, z) indicate three-dimensional position, e.g. forward and back (y-axis), left and right (x-axis), up and down (z-axis), and three rotation parameters (pitch, roll, yaw) indicate orientation of the tool or object, e.g. rotation about the x-axis (pitch), rotation about the y-axis (roll), and rotation about to the z-axis (yaw). Various systems are available for determining the spatial position and orientation of an object. One such system includes use of a mechanical arm to track the location of a medical tool or probe which can be used to further determine the location of a target. In order to locate the target, the tool or probe can be affixed to the mechanical arm having a known reference position. A computer system tracks the tool or probe while an operator repositions the tool or probe along with the mechanical arm. The geometry of the mechanical arm is known such that movement of the tool or probe in conjunction with the mechanical arm provides the computer system continuous position information regarding the tool or probe. In an invasive procedure, the tool or probe can have a fixed length. Thus, contacting the target with the end of the tool can provide a position location of the target. In a noninvasive procedure, a probe, such as an ultrasound device, can be used to locate both the position and the orientation of the target. Recognized, however, is that the mechanical arm can be cumbersome or difficult for the operator to work with. Additionally, the mechanical arm can be subject to inaccuracies caused by component imperfections due to manufacturing tolerances and mechanical wear and by the effects of gravity on the arm, which to varying degrees depending upon the arm orientation, can act to offset the arm position from that calculated.

Another such system can include either sonic, optical, radio frequency, or even magnetic detectors affixed to the tool or object and active radiating emitters and a computer system or unit. In order to determine the six degrees of freedom of the object or tool, generally, at least three points on the object must be detected. Recognized, however, is that the circuitry involved can be cumbersome or can require modification to the tool or object. For example, generally, wiring from the detectors used to transfer the received signal to a decoder and to the computer system or unit must be affixed on or adjacent to the tool or object. Often, such wiring provides an obstacle to the operator. Also, most detectors typically function by detecting the time, frequency, or amplitude differential between the various detectors in receiving usually at least a pair of external source signals from the emitters in order to determine the spatial position of the tool or object. Thus, the emitter or detector circuitry must, by its nature, be complicated in order to provide for the ability to separately activate each detector.

A similar system can instead include either sonic, optical, or radio frequency emitters affixed to the tool or object and receivers such as sonic, optical, or radio frequency sensors, and a computer system or unit. As described with respect to the use of detectors, in order to determine the six degrees of freedom of the object or tool, at least three points on the object typically must generally be detected. The emitters can be either active or passive. Active emitters, however, are subject to the same wiring interference as that of detectors. Wiring generally supplies encoded signals to each of the emitters which function as markers and which are either activated in sequence or provide sonic, optical, or radio frequency signals on different frequencies. Thus, the emitter or external detector circuitry must therefore, by their nature, be complicated in order to provide for the ability to separately activate each emitter. To reduce the complication and the emitter or external detector circuitry, the emitters can instead function simultaneously emitting the same type of signal. Where the emitters produce such same type signal, however, the emitters are subject to co-emitter interference when the emitters overlap each other with respect to the field of view of the sensors.

Unlike active emitters, passive emitters are generally in the form of a reflector and do not necessarily suffer the same wiring limitations. Passive emitters are becoming the preferred type of emitter as they can be installed on virtually any type of object or tool to provide a relative location of the object or tool or a portion, thereof. Passive emitters supply their signal via active radiating external emitters positioned within view of the passive emitters. The signal from the active emitters is reflected by the passive emitters. The circuitry involved with passive emitters is generally less complicated as they tend to function simultaneously, each emitting or reflecting the same type of signal. Passive emitters, however, are correspondingly also subject to co-emitter interference when the emitters overlap each other with respect to the field of view of the sensors.

Both active and passive emission techniques operate by projecting a geometric representation or extension of the object or tool formed by the emitters onto the field of view of a pair of spaced sensors. Various implementations of sensors have been used, the most popular being the use of two cameras positioned spaced apart a known distance and angled in the general direction of the object or tool such that the three-dimensional position of the object or tool can be obtained by triangulation from the positions of the emitters. For example, a camera or opti-electrical motion measurement system, known as the Polaris®, by Northern Digital Inc., Ontario Canada, has been used for triangulating the position of optically trackable tools.

Specifically, a computer system, using mathematical processing, can determine the three dimensional coordinates of each one of the emitters associated with the object or tool. The position of each of the emitters can be used to determine the position of the object or tool relative to a three dimensional coordinate system centered at a preselected point in space, typically at a point fixed relative to the sensors. The positional relationship to each other of each of the emitters associated with the object or tool can be utilized to further determine the orientation in space of the object or tool. Generally, at least three of the emitters must be detected and must be unobscured by any adjacent emitters. Additionally, the sensors generally require the emitters to be a minimum distance, for example, 3-5 cm apart. Theoretically, such systems should provide three unobstructed emitters for most of a sphere created by the six degrees of freedom. One of the more modern types of passive emission system utilizes passive retro-reflectors which can be affixed to the object or tool and which reflect directly back to a pair of active emitter arrays adjacent a pair of optical sensors. This type of system allows the optical sensors to be positioned relatively close together.

Recognized by the Applicant is that the active systems using a single frequency, wavelength, and amplitude, and the passive systems which inherently do so, are subject to significant field of view limitations. For example, where the three or more emitters are positioned on the tool or object, the emitters will tend to line-up or occlude each other for a large segment of the sphere created by the six degrees of freedom. Where emitter interference occurs, all emitters involved are generally deemed by the computer to be unreliable or unusable. If one or more of those emitters are required by the computer to determine the position of the tool, the tracking of the tool will be lost until three unobstructed emitters are reacquired in the field of view of the sensors. Though in some instances, the prior art has tried to "wallpaper" the tool or an object with upwards of 24 emitters in order to have at least three unobscured emitters, still elusive has been a system, tracker, or related methods for providing at least three unobscured emitters throughout substantially the entire sphere created by the six degrees of freedom.

Also recognized by the Applicant is that mounting the emitters directly to a tool or object frequently exacerbates any existing obstruction problems. For example, if the emitters are mounted directly on the handle of a tool, the operator will have to try to work around the emitters to cover or otherwise obscure them. Additionally recognized by the Applicant is that so as not of interest on a tool or object can be directly determined by the orientation of the emitters. Thus, any mount positioned on the tool or object to carry the emitters must be precisely ed in the correct juxaposition in order to prevent calculation errors. Such mount should also be capable of being easily and quickly disconnected and accurately and repeatably reconnected. For a tool, such as an ultrasound device, which may be frequently separated from the mount in order to clean, service, or inspect the device, it may be imperative to productivity to have such a connection.

SUMMARY OF THE INVENTION

In view of the foregoing, embodiments of the present invention advantageously provide a system, tracker, and methods related to use of a tracker that provides a user the ability to track both the three-dimensional position and the orientation of a movable object over substantially all possible object orientations without significant occlusion. Advantageously, embodiments of the present invention also provide a tracker that is size scalable in order to meet requirements of the movable object and to control the accuracy of the tracking solution. Advantageously, embodiments of the present invention also provide a geometric indicator or emitter design which forms a plurality of preferably dissimilar geometric figures composed of three or more indicators or emitters preferably in the form of retro-reflective spheres that are readily distinguishable by an optical detector or camera system. Advantageously, embodiments of the present invention also provide flanges and other "obfuscating" structures that occlude or prevent coincident alignment of specific optical indicators from view by the optical detector or camera system. This prevents indicators which comprise one geometric figure from becoming juxtaposed or optically coincident with indicators which form another geometric figure, which would result in the indicators being unusable to the optical detector or camera system, and thus loss of a tracking solution. Advantageously, embodiments of the present invention incorporate a mechanical quick disconnect to allow ready removal from the movable object being tracked while still providing positioning functionality and which compels the tracker into the correct mounting position on the movable object, to prevent use of the tracker in an incorrect state.

Embodiments of the present invention provide a system for tracking a three-dimensional position and an orientation of a movable object. The system generally includes a tracker having an optically trackable body adapted to connect to the movable object. A plurality of optical indicators are connected or mounted to the optically trackable body to form a plurality of preferably dissimilar geometric figures. Separating means, such as, for example, a plurality of obfuscating flanges is provided, to optically separate each of the plurality of optical indicators from each other to prevent each of the plurality of indicators from becoming optically coincident with another one of the plurality of indicators when viewed along a collinear viewing path extending directly through either pair of the plurality of indicators. The system also includes an apparatus to track a trackable body having an optical detector to simultaneously detect the three-dimensional position of at least three of the plurality of optical indicators, and a determiner to determine the three-dimensional position and orientation of the optically trackable body from the position of the optical indicators, and thus, the three-dimensional position and orientation of the movable object.

More specifically, in an embodiment of the present invention the system includes a tracker having a plurality of separate and spaced apart optical indicators, advantageously in the form of optical retro-reflective spheres mounted or connected to an optically trackable body. The plurality of indicators are adapted to be optically tracked over a subset of possible movable object orientations. The plurality of indicators have a preferably dissimilar preselected segment length between each pair combination, whereby a plurality of combinations of at least three of the plurality of indicators define a plurality of geometric figures. The three-dimensional location of the indicators and the orientation of the geometric figures provide three-dimensional positional data and orientation data of the movable object.

The optically trackable body having the plurality of indicators mounted thereto includes a proximal body end portion, a distal body end portion, a medial body portion connected to and extending between the proximal body end portion and the distal body end portion, and a longitudinal axis. The optically trackable body also includes separating means for optically separating each of the plurality of indicators from each other to prevent each of the plurality of indicators from becoming optically coincident with another one of the plurality of indicators when viewed along a plurality of preselected viewing paths extending directly through each pair combination of the plurality of indicators to thereby enhance optical detection of the plurality of indicators to thereby determine the positional location and orientation of the movable object.

In an embodiment of the present invention, the separating means includes a plurality of obfuscators provided, e.g., by a plurality of obfuscating flanges. The plurality of obfuscating flanges can include a plurality of longitudinal medial body portion obfuscating flanges sized and positioned substantially parallel to and spaced apart from the longitudinal axis of the medial body portion of the optically trackable body. The plurality of medial body portion obfuscating flanges optically separate each indicator of the plurality of indicators mounted to the medial body portion of the optically trackable body from each adjacent indicator of the plurality of indicators also mounted to the medial body portion of the optically trackable body. This prevents or significantly reduces a possibility of each indicator of the plurality of indicators, mounted to the medial body portion of the optically trackable body, becoming optically coincident with each respective adjacent indicator of the plurality of indicators, also mounted to the medial body portion of the optically trackable body, when viewed along either of the plurality of preselected viewing paths extending directly through each respective pair of the plurality of indicators mounted to the medial body portion of the optically trackable body.

The plurality of obfuscating flanges can also include a radial medial body portion obfuscating flange positioned substantially axially parallel with the longitudinal axis of the medial body portion of the optically trackable body. The radial medial body portion obfuscating flange is positioned and sized to optically separate each indicator of the plurality of indicators mounted to the distal body end portion of the optically trackable body from each indicator of the plurality of indicators connected or mounted to the medial body portion of the optically trackable body. This prevents, or significantly reduces a possibility, each indicator of the plurality of indicators connected or mounted to the distal body portion of the optically trackable body from becoming optically coincident with either indicator of the plurality of indicators connected or mounted to the medial body portion of the optically trackable body, when viewed along either of the plurality of preselected viewing paths extending directly through each indicator of the plurality of indicators connected or mounted to the distal body portion of the optically trackable body and either indicator of the plurality of indicators connected or mounted to the medial body portion of the optically trackable body.

The distal body end portion of the optically trackable body, for example, can have a pair of adjacent indicators connected or mounted thereto. In such configuration, the plurality of obfuscating flanges can include a distal body end portion obfuscating flange positioned substantially axially perpendicular to the longitudinal axis of the medial body portion of the optically trackable body. The distal body end portion obfuscating flange is positioned and sized to optically separate a first indicator of the pair of indicators connected or mounted to the distal body end portion of the optically trackable body from a second indicator of the pair of indicators connected or mounted to the distal body portion of the optically trackable body. This can prevent the first indicator of the pair of adjacent indicators connected or mounted to the distal body end portion of the optically trackable body from becoming optically coincident with the second indicator of the pair of indicators connected or mounted to the distal body end portion of the optically trackable body, when viewed along either of the plurality of preselected viewing paths extending directly through the first and second indicators of the pair of adjacent indicators connected or mounted to the distal body end portion of the optically trackable body.

The optically trackable body can also include an interior mount recess inwardly extending from the proximal body end portion into the medial body portion. The interior mount recess is adapted to slidably receive at least portions of a mounting connector adapted to connect the optically trackable body to the movable object. The medial body portion of the optically trackable body can further include a mounting connector retention recess extending between outer surface portions of the medial body portion and inner surface portions of the interior mount recess and positioned substantially normal to the interior mount recess to house at least portions of a mounting connector retention member provided to fixedly retain the mounting connector within the interior mount recess, when so positioned. Advantageously, this can form a quick disconnect.

The proximal body end portion of the optically trackable body can further include a proximal body end mounting extension connected to and integral with the proximal body end portion of the body. The proximal body end mounting extension can extend substantially perpendicular to and outwardly from the longitudinal axis of the optically trackable body. The proximal body end mounting extension can have a substantially flat planer proximal surface adapted to interface with a corresponding planer surface of either the movable object or a movable object mounting interface of an intermediate mount. Advantageously, this allows for ease of positioning or mounting the optically trackable body to the movable object.

The system also includes an apparatus to track a trackable body or camera subsystem including an optical detector and a determiner. The optical detector has an optical detector body positioned separate and spaced apart from the optically trackable body at a predetermined three-dimensional sensor reference location. The optical detector preferably includes a pair of separate and spaced apart optical receivers connected to the optical detector body, each having a field of view and being adapted to receive optical energy emitted or reflected by each of the plurality of optical indicators when positioned in the field of view. The optical receivers can detect the three-dimensional sphere position of each of the plurality of indicators when positioned simultaneously within the field of view of both of the optical receivers to produce a plurality of position signals representing such three-dimensional indicator positions. When the plurality of indicators are in the form of optical retro-reflective spheres, the optical detector can include a pair of infrared illuminators. A first illuminator is positioned adjacent to one of the pair of separate and spaced apart optical receivers and a second illuminator is positioned adjacent to the other of the pair of separate and spaced apart optical receivers to selectively illuminate each of the plurality of optical retro-reflective spheres when positioned in the field of view of the respective adjacent optical receiver. This provides the requisite optical energy necessary to view the optical retro-reflective spheres within the field of view of the respective adjacent optical receiver.

The determiner is in communication with the optical detector and is responsive to the plurality of position signals produced by the optical detector to determine the three-dimensional indicator position of each of the plurality of indicators when positioned simultaneously within the field of view of both of the optical receivers of the optical detector. The determiner has a memory associated therewith to store a table of definitions containing unique segment lengths between each pair of the plurality of optical indicators. Responsive to the segment lengths, the determiner can determine which of the plurality of geometric figures is in view of the optical receivers. Once the particular geometric figure is identified, by determining the orientation of the particular geometric figure, the determiner can then further determine the three-dimensional position and the orientation of the tracker, and thus, the movable object.

Advantageously, also provided are methods for tracking a position and an orientation of a movable object. For example, in an embodiment of the present invention, a method for tracking a position and an orientation of a movable object includes connecting a plurality of indicators to an optically trackable body to form a plurality of geometric figures and connecting the optically trackable body to the movable object. The optically trackable body includes at least one obfuscating flange sized and positioned to optically separate, at a minimum, a first of the plurality of indicators from a second of the plurality of indicators when viewed along a preselected viewing path. An optical detector can be used to view one of the plurality of geometric figures when positioned in its field of view. A determiner can then be used to identify which one of the plurality of geometric figures is positioned in a field of view of the optical detector. Analysis of the position and orientation of the identified geometric figure in the field of view of the optical detector can then be used to determine the position and orientation of the movable object.

By continuously analyzing the position and orientation of the geometric figures, the position and orientation of the movable object can be continuously re-determined while the geometric figures remains in the field of view of the optical detector. The position and orientation of the movable object can be continuously tracked through various rotations of the movable object by obfuscating a first of the plurality of indicators as it leaves the field of view of the optical detector to prevent the first of the plurality of indicators from becoming optically coincident with a second of the plurality of indicators. This allows the optical detector to thereby replace the one of the plurality of geometric figures positioned in the field of view of the optical detector with another one of the plurality of geometric figures positioned in the field of view of the optical detector. This second of the plurality of figures can then be tracked until replaced with a third of the plurality of figures.

Also for example, in an embodiment of the present invention, a method for tracking a position and an orientation of a movable object includes connecting an optically trackable body having a plurality of indicators to the movable object, the optically trackable body having a first obfuscating flange sized and positioned to optically separate a first of the plurality of indicators from a second of the plurality of indicators and a second obfuscating flange sized and positioned to optically separate the second of the plurality of indicators from a third of the plurality of indicators. During movement of the movable object, and thus the trackable body, the first obfuscating flange is positioned to obfuscate the first of the plurality of indicators to prevent the first of the plurality of indicators from becoming optically coincident with the second of the plurality of indicators. An optical detector which can simultaneously detect the position of multiple indicators is positioned to view a subset of the plurality of indicators in a field of view of the optical detector to identify which of the plurality of indicators are positioned in a field of view of the optical detector. Having detected and identified the plurality of indicators, the position of at least three of the plurality of indicators in the field of view of the optical detector can then be analyzed to determine the position and orientation of the movable object, allowing tracking of the move object.

Advantageously, also provided are methods for enhancing detection of a trackable body. For example, in an embodiment of the present invention, a method for enhancing detection of a trackable body includes positioning at least one obfuscating flange on a trackable body having a plurality of optical indicators to optically separate a first of the plurality of optical indicators from a second of the plurality of optical indicators. The positioning of the at least one obfuscating flange allows for inhibiting the first of the plurality of optical indicators from becoming optically coincident with the second of the plurality of optical indicators when viewing the trackable body along a preselected viewing path by obfuscating the first of the plurality of optical indicators from the second of the plurality of optical detectors with the at least one obfuscating flange.

Advantageously, embodiments of the present invention include a tracker having a compact lightweight design, that is easy to install to a movable object, inexpensive to manufacture, and is relatively simple to use. Advantageously, the tracker can be easily removed or interchanged with other movable objects enabling a variety of different applications. Advantageously, the tracker has an intelligent juxtaposition of optical indicators and obfuscators that allow optical tracking of the tracker, with few exceptions, at substantially any given orientation of the tracker. The optical detector or camera system is provided enough optical indicators to identify and locate the tracker without those indicators interfering with each other. Advantageously, the size, shape, and juxtaposition of the indicators and the obfuscating flanges of the tracker allow for utilization of nearly the full potential of various optical detector or cameras systems having a hemispherical or spherical field of view. Advantageously, a single tracker can be used with movable objects of various size and shape. Advantageously, the tracker is scalable in that the longitudinal length and/or lateral width of the optically trackable body can be increased thus, the size of the lengths between optical indicators can be increased which improves tracking solution accuracy. Advantageously a position determiner can be provided a trackable body tag, such as a serial number, preferably assigned to the tracker at the time of manufacture, to allow automated calibration of the tracker with a specifically identified movable object mount and/or the movable object. Advantageously, regarding medical implementation of the tracker, the optically trackable body includes such versatility such that it can be connected to a treatment table of a radiation therapy treatment machine to allow a user to align a patient for radiation delivery. Additionally, at the time of manufacture, the movable object mount can be fitted to the movable object, such as an ultrasound probe, and calibrated to the movable object mount to further maximize precision of the mounting.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 3 is an exploded perspective view of a portion of a system for tracking position and orientation of a movable object according to an embodiment of the present invention;

FIG. 4 is perspective view of an optically trackable body for tracking position and orientation of a movable object according to an embodiment of the present invention;

FIG. 6 is a sectional view of a tracker for tracking position and orientation of a movable object taken along the 6-6 line of FIG. 5 according to an embodiment of the present invention;

FIG. 7 is a perspective view of an optically trackable body for tracking position and orientation of a movable object taken along the 7-7 line of FIG. 4 according to an embodiment of the present invention;

FIG. 8 is a perspective view of an optically trackable body for tracking position and orientation of the movable object taken along the 8-8 line of FIG. 4 according to an embodiment of the present invention;

FIG. 9 is a perspective view of an optically trackable body for tracking position and orientation of the movable object taken along the 9-9 line of FIG. 4 according to an embodiment of the present invention;

FIG. 10 is a perspective view of an optically trackable body for tracking position and orientation of the movable object taken along the 10-10 line of FIG. 9 according to an embodiment of the present invention;

FIG. 11 is a perspective view of an optically trackable body for tracking position and orientation of the movable object taken along the 11-11 line of FIG. 10 according to an embodiment of the present invention;

FIG. 12 is a perspective view of an optically trackable body for tracking position and orientation of the movable object taken along the 12-12 line of FIG. 11 according to an embodiment of the present invention;

DETAILED DESCRIPTION

Figure 1:
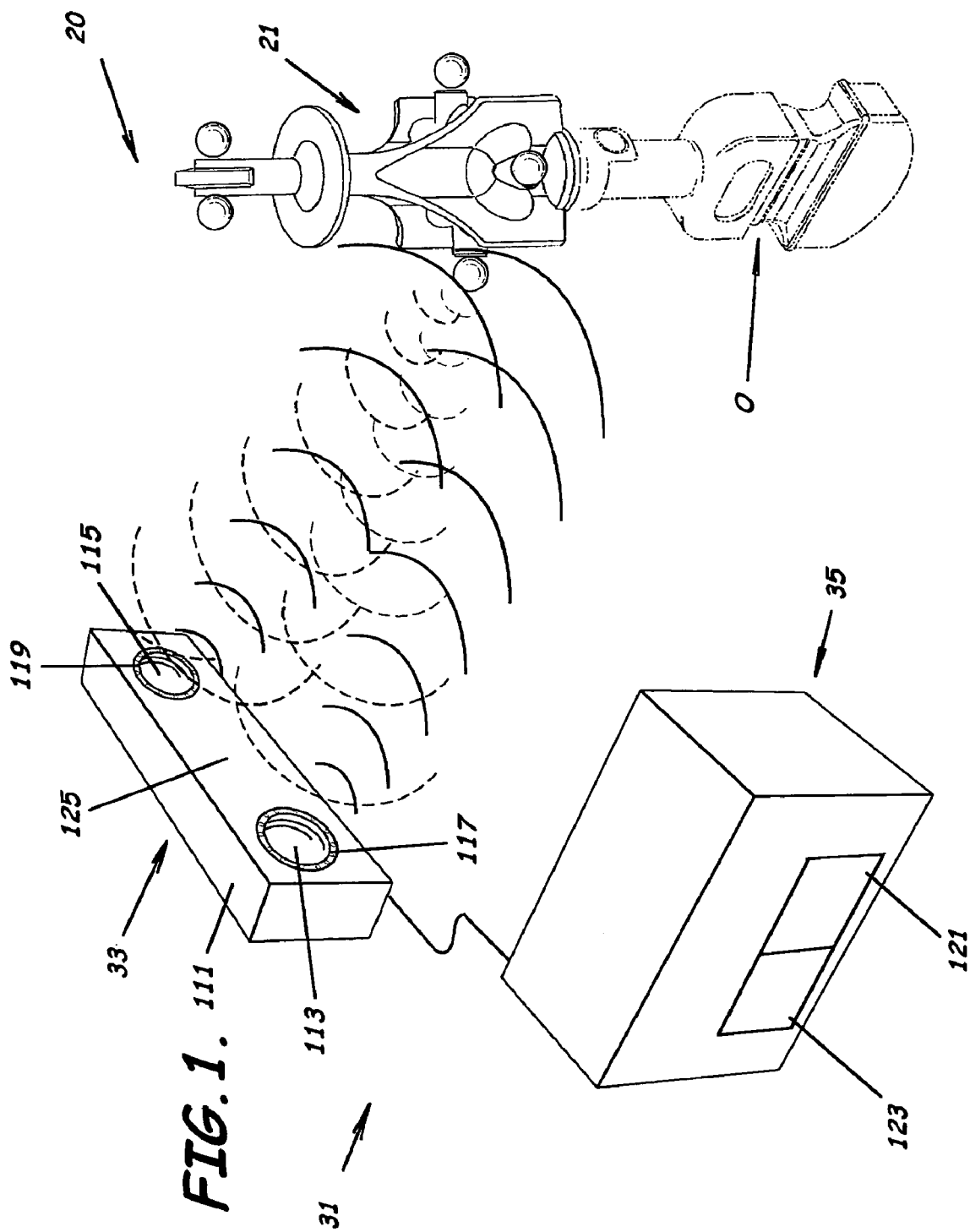
FIG. 1 is a system for tracking position and orientation of a movable object, according to an embodiment of the present invention.

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments. Note, the term "indicator" as used herein refers to either active or passive emitters including but not limited to optically retro-reflective spheres.

As illustrated in FIGS. 1-14, embodiments of the present invention advantageously provide a system 20, tracker 21, and methods for tracking a three-dimensional position and an orientation of a movable object O. As perhaps best shown in FIGS. 1-3, the system 20 includes a tracker 21 having an optically trackable body 23 connected to the movable object O, illustrated as an ultrasound wand. A plurality of optical indicators, such as optically retro-reflective spheres 25, are connected or mounted to the optically trackable body 23 to form a plurality of preferably dissimilar geometric figures F, such as, for example, that illustrated in FIG. 2. Separating means such as, for example, a plurality of obfuscators provided by variously positioned obfuscating flanges 27 (FIG. 2), obfuscating projections, or other obfuscating obstacles, known to those skilled in the art, optically separate each of the plurality of optical retro-reflective spheres 25 from each other to prevent each of the plurality of retro-reflective spheres 25 from becoming optically coincident with another one of the plurality of retro-reflective spheres when viewed along a viewing path, such as, for example, viewing paths P1-P3 (FIG. 5) which extend through adjacent spheres 25. The system 20 also includes an apparatus to track a trackable body or camera subsystem 31 including an optical detector 33 implemented to simultaneously detect the three-dimensional position of at least three of the plurality of optical retro-reflective spheres 25, and a determiner 35 implemented to determine the three-dimensional position and orientation of the optically trackable body 23 from the detected three-dimensional position of the optical retro-reflective spheres 25, and thus, the three-dimensional position and orientation of the movable object O.

More specifically, as shown in FIGS. 3-13, the system 20 includes a tracker 21 having a plurality of separate and spaced apart optical indicators, preferably in the form of optical retro-reflective spheres 25 mounted or connected to an optically trackable body 23. The retro-reflective spheres 25 can be formed of retro-reflective prisms (not shown), as understood by those skilled in the art, that reflect light that strikes them in the exact opposite direction. The optically trackable body 23 correspondingly includes a plurality of separate and spaced apart indicator mounts 29 (FIG. 4) to connect or mount the optical retro-reflective spheres 25 to the optically trackable body 23. The plurality of optically retro-reflective spheres 25 are adapted to be optically tracked over a subset of possible orientations of the movable object O. The plurality of retro-reflective spheres 25 preferably have a dissimilar preselected segment length S (FIG. 2) between each pair combination. A plurality of combinations of typically at least three of the plurality of retro-reflective spheres 25 can define a plurality of geometric figures F, such as, for example, that geometric figure illustrated in FIG. 5. Further, each sphere 25 in the plurality of the retro-reflective spheres 25 can be positioned to form at least two of the plurality of geometric figures F to reduce a selected number of spheres 25 required.

The three-dimensional location of the retro-reflective spheres 25 and the orientation of each of the geometric figures can provide three-dimensional positional information and orientation information of the optically trackable body 23, and thus, the movable object O. In the preferred implementation, the geometric figures F are readily (or uniquely) distinguishable by an apparatus to track a trackable body or camera subsystem 31 (described later). The plurality of retro-reflective spheres 25 can be positioned such that by the time one of the geometric figures F is no longer visible to the apparatus or camera subsystem 31, another of the plurality of geometric figures F becomes visible to the optical tracking system or camera subsystem 31. The position and orientation of each identified geometric figure F directly translates to that of the optically trackable body 23, and thus, the movable object O.

Note, although the plurality of indicators can take the form of other locatable indicators, optical retro-reflective spheres 25 are preferred as they advantageously negate the requirement for supplying the tracker 21 with electric power or illumination such as that required by indicators in the form of light emitting diodes or fiber optics. Advantageously, this reduces the weight and complication of the tracker 21 and helps prevent the tracker 21 from interfering with an operator or medical patient during use, if so implemented. This also improves ease of manufacture with high tolerances, an important feature where the operator requires the utmost precision. Further, the optical retro-reflective spheres 25 are preferred due to their wide field of view which allows detection at a wide range of viewing angles, exceeding 180 degrees. This allows for a smaller trackable body 23 with less required spheres 25.

Figure 5:
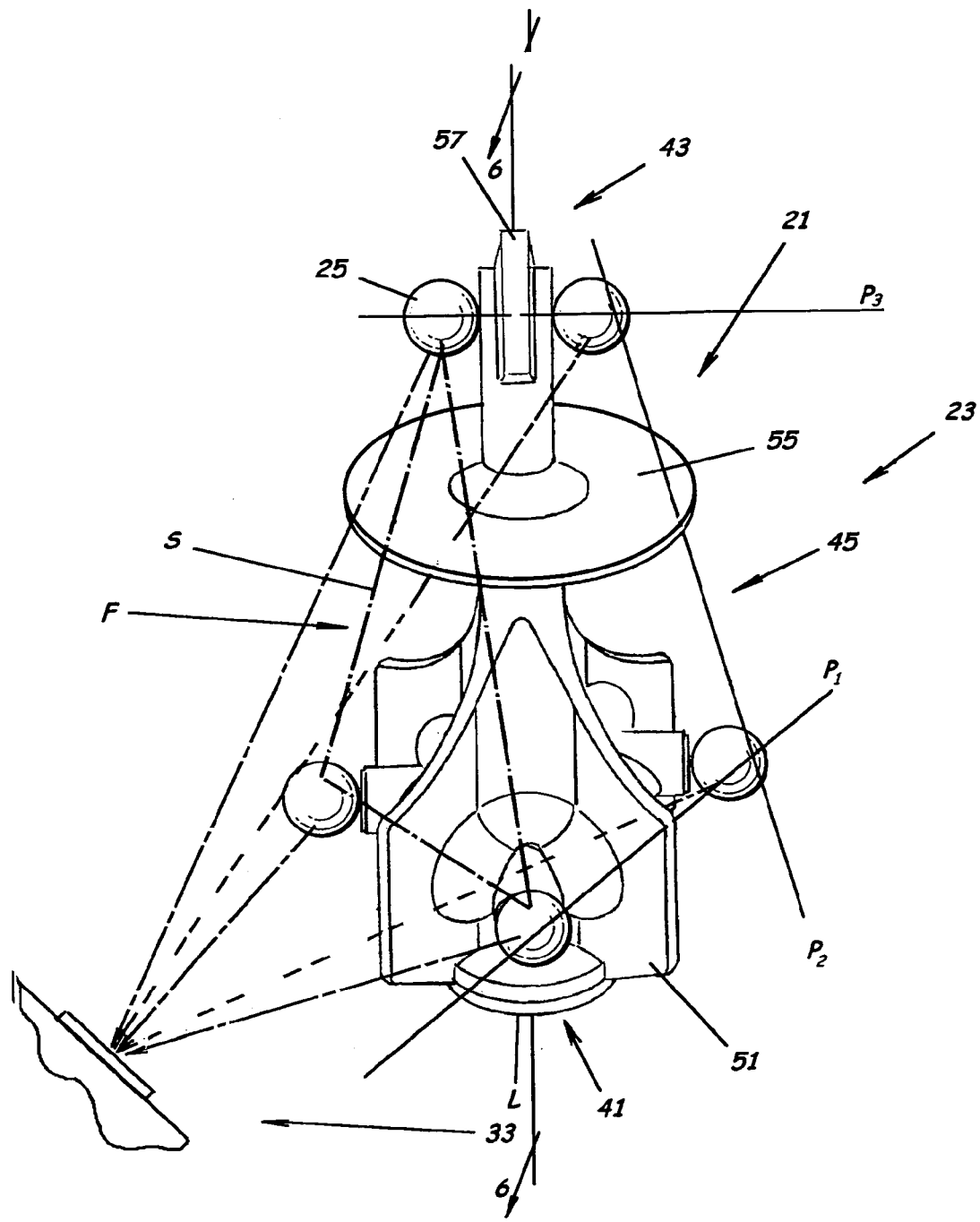
FIG. 5 is a perspective view of a portion of a system for tracking position and orientation of a movable object according to an embodiment of the present invention.

As shown in FIGS. 4-6, the optically trackable body 23 includes a proximal body end portion 41, a distal body end portion 43, a medial body portion 45 connected to and extending between the proximal body end portion 41 and distal body end portion 43, and a longitudinal axis L (FIG. 5). As perhaps best shown in FIGS. 9-12, the plurality of indicator mounts 29 on the medial body portion 45 can be equally radially spaced apart but longitudinally staggered in unequal lengths to produce the preselected segment lengths S (FIG. 5). Each of the indicator mounts 29 can include an optical indicator mounting recess 47 or other means such as various forms of fasteners or connectors, known to those skilled in the art, for connecting each respective one of the plurality of spheres 25 or other optical indicators to a corresponding plurality of the indicator mounts 29.

The optically trackable body 23 also includes separating means (described below) for optically separating each of the plurality of optical retro-reflective spheres 25 from each other to prevent each of the plurality of retro-reflective spheres 25 from becoming optically coincident with another one of the plurality of retro-reflective spheres 25 when viewed along a viewing path extending directly through either adjacent pair combination of the plurality of retro-reflective spheres 25. This separating means can serve to enhance optical detection of the plurality of retro-reflective spheres 25 to thereby further enhance determination of the positional location and orientation of the optically trackable body 23, and thus, the movable object O.

The separating means can include various forms known and understood by those skilled in the art, but are preferably in the form of a plurality of variously shaped and positioned obfuscators including various forms of flanges, projections, separators, attachments, or other types of obstacles positionable between a pair of retro-reflective spheres 25. For example, as perhaps best shown in FIGS. 4, 5 and 7, the optically trackable body 23 can include a plurality of longitudinal medial body portion obfuscating flanges 51 sized and positioned substantially parallel to and spaced apart from the longitudinal axis L of the medial body portion 45 of the optically trackable body 23. The plurality of medial body portion obfuscating flanges 51 are of sufficient longitudinal length and radial width to optically separate each retro-reflective sphere 25 of the plurality of retro-reflective spheres 25 mounted to the medial body portion 45 of the optically trackable body 23 from each adjacent retro-reflective sphere 25 of the plurality of retro-reflective spheres 25 also mounted to the medial body portion of the optically trackable body 23. This prevents, or significantly reduces, possibilities or risks of either retro-reflective sphere 25 of the plurality of retro-reflective spheres 25 mounted to the medial body portion 45 of the optically trackable body 23 from becoming optically coincident with an adjacent retro-reflective sphere 25 of the plurality of retro-reflective spheres 25 also mounted to the medial body portion 45 of the optically trackable body 23, when viewed along a preselected (collinear) viewing path, such as, for example, viewing path P1. Note, the medial body portion obfuscating flanges 51 can be of various geometric designs as long as they are radially short enough so that when observed or viewed such that a reference retro-reflective sphere 25 on the medial body portion 45 of the optically trackable body 23 is "pointing" directly at an observer (e.g. FIG. 5), the medial body portion obfuscating flanges 51 on either side of the reference retro-reflective sphere 25 do not obscure adjacent retro-reflective spheres 25, but radially and longitudinally long enough so that when observed such that a reference medial body portion obfuscating flanges 51 is "pointing" directly at the observer, the adjacent obfuscating flanges 51 obscure adjacent retro-reflective spheres 25 positioned "behind" the adjacent obfuscating flanges 51.

Because the adjacent spheres 25 are prevented from becoming visually coincident with each other of the spheres 25, and thus, prevented from visually interacting with each other with respect to an outside observer, the spheres 25 forming the various unique or different geometric figures are viewable by the apparatus or camera subsystem 31 such that the apparatus or camera subsystem 31 should generally not find any of the spheres 25 unusable due to coincidence with any of the other spheres 25 in the determination of which of the various different geometric figures F is in the field of view of the optical tracking system or camera subsystem 31. Note, although more than one different geometric figure F can be in the field of view, normally only one would be selected.

As perhaps best shown in FIGS. 4, 5, and 8, the optically trackable body 23 can also include a preferably annular medial body portion obfuscating flange 55 positioned substantially axially parallel with the longitudinal axis L of the medial body portion 45 of the optically trackable body 23.

The radial medial body portion obfuscating flange 55 is positioned and sized to optically separate each retro-reflective sphere 25 of the plurality of retro-reflective spheres 25 mounted to the distal body end portion of the optically trackable body 23 from each adjacent retro-reflective sphere 25 of the plurality of retro-reflective spheres 25 mounted to the medial body portion of the optically trackable body 23. This prevents each retro-reflective sphere 25 of the plurality of retro-reflective spheres 25 mounted to the distal body portion 43 of the optically trackable body 23 from becoming optically coincident with each retro-reflective sphere 25 of the plurality of retro-reflective spheres 25 mounted to the medial body portion 45 of the optically trackable body 23, when viewed along a preselected viewing path, such as, for example, viewing path P2 (FIG. 5). Note, flange 55 need not be annular, but may instead be other geometric shapes.

As shown in FIG. 5, the distal body end portion 43 of the optically trackable body 23 can have a pair of adjacent retro-reflective spheres 25 mounted thereto. In such configuration, as perhaps best shown in FIGS. 4, 5 and 8, the optically trackable body 23 can include a distal body end portion obfuscating flange 57 positioned substantially axially perpendicular to the longitudinal axis L of the medial body portion 45 of the optically trackable body 23. The distal body end portion obfuscating flange 57 is positioned and sized to optically separate a first retro-reflective sphere 25 of the pair of retro-reflective spheres 25 mounted to the distal body end portion of the optically trackable body 23 from a second retro-reflective sphere 25 of the pair of retro-reflective spheres 25 mounted to the distal body portion of the optically trackable body 23. This can prevent the first retro-reflective sphere 25 of the pair of adjacent retro-reflective spheres 25 mounted to the distal body end portion 43 of the optically trackable body 23 from becoming optically coincident with the second retro-reflective sphere 25 of the pair of retro-reflective spheres 25 mounted to the distal body end portion 43 of the optically trackable body 23, when viewed along a preselected viewing path, such as, for example, viewing path P3. Note, flange 57 need not be annular, as illustrated, but may instead be other geometric shapes.

Advantageously, the combination of the obfuscating flanges 51, 55, and 56, can also serve to help prevent the plurality of retro-reflective spheres 25 from being inadvertently adulterated by the operator. Additionally, the combination of the positioning of the plurality of retro-reflective spheres 25 and size and position of obfuscating flanges 51, 55, and 56 can be adjusted to be implemented with a larger or smaller optically trackable body 23. Thus, this combination allows for manufacturing the tracker 21 to allow various degrees of three-dimensional position and orientation accuracy and various degrees of ergonomic design. For example, increasing the size of the optically trackable body 23, thereby extending the segment lengths S, can result in improved accuracy. Also, for example, the medial body portion obfuscating flange 55 can be positioned either closer to the distal body end portion 43 or the proximal body end portion 41, and still maintain functionality. Maintaining functionality of the medial body portion obfuscating flange 55 merely requires adjusting the radial length of at least the portion of the obfuscating flange 55 that prevents coincidence of the spheres 25 positioned on the medial body end portion 45 and the spheres 25 positioned at or adjacent the distal body end portion 43. For example, for an optically trackable body 23 of a given length, positioning the medial body portion obfuscating flange 55 closer to the distal body end portion 43 should generally allow a reduction in the radial length of the medial body portion obfuscating flange 55.

Figure 2:
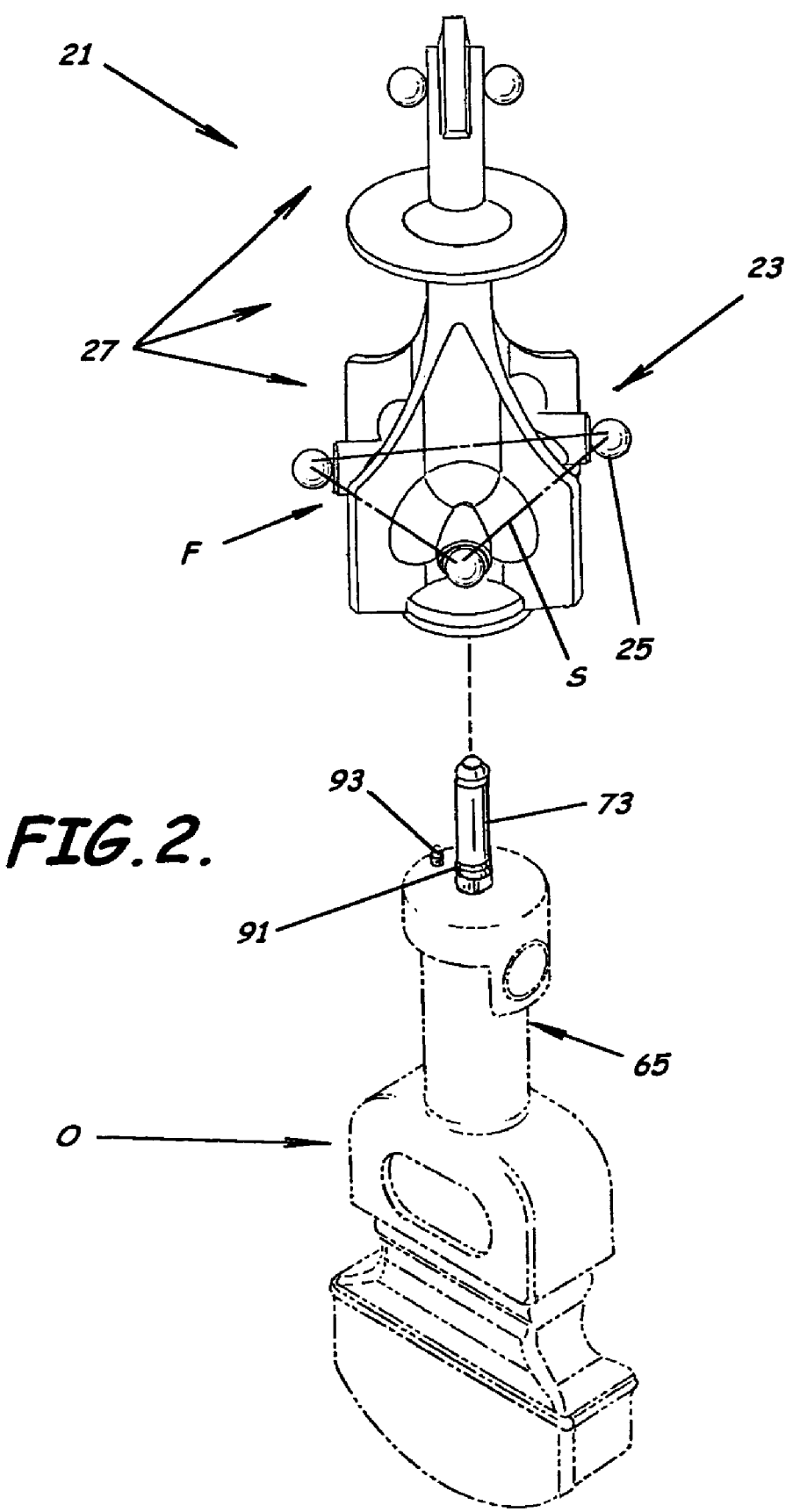
FIG. 2 is an exploded perspective view of a portion of a system for tracking position and orientation of a movable object according to an embodiment of the present invention.
Figure 13:
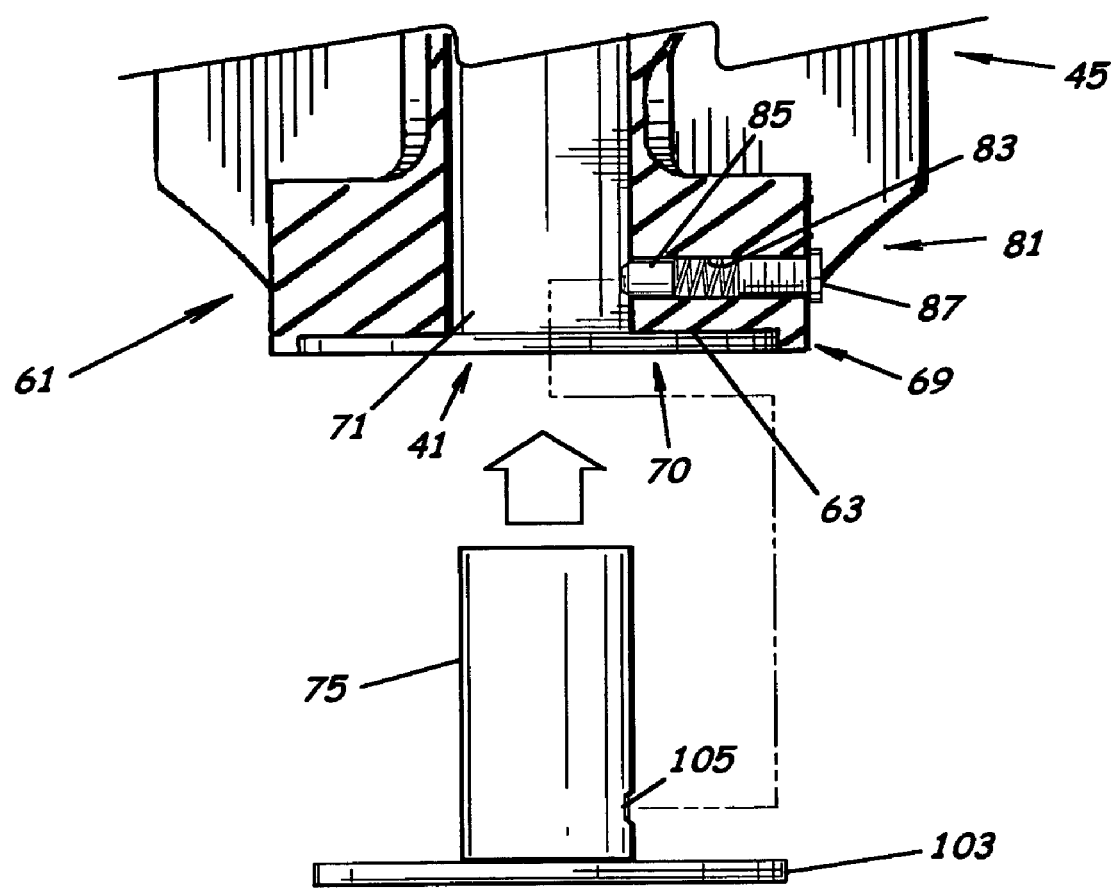
FIG. 13 is a fragmentary and exploded view of a tracker for tracking position and orientation of a movable object having portions thereof broken away for clarity according to an embodiment of the present invention.
Figure 14:
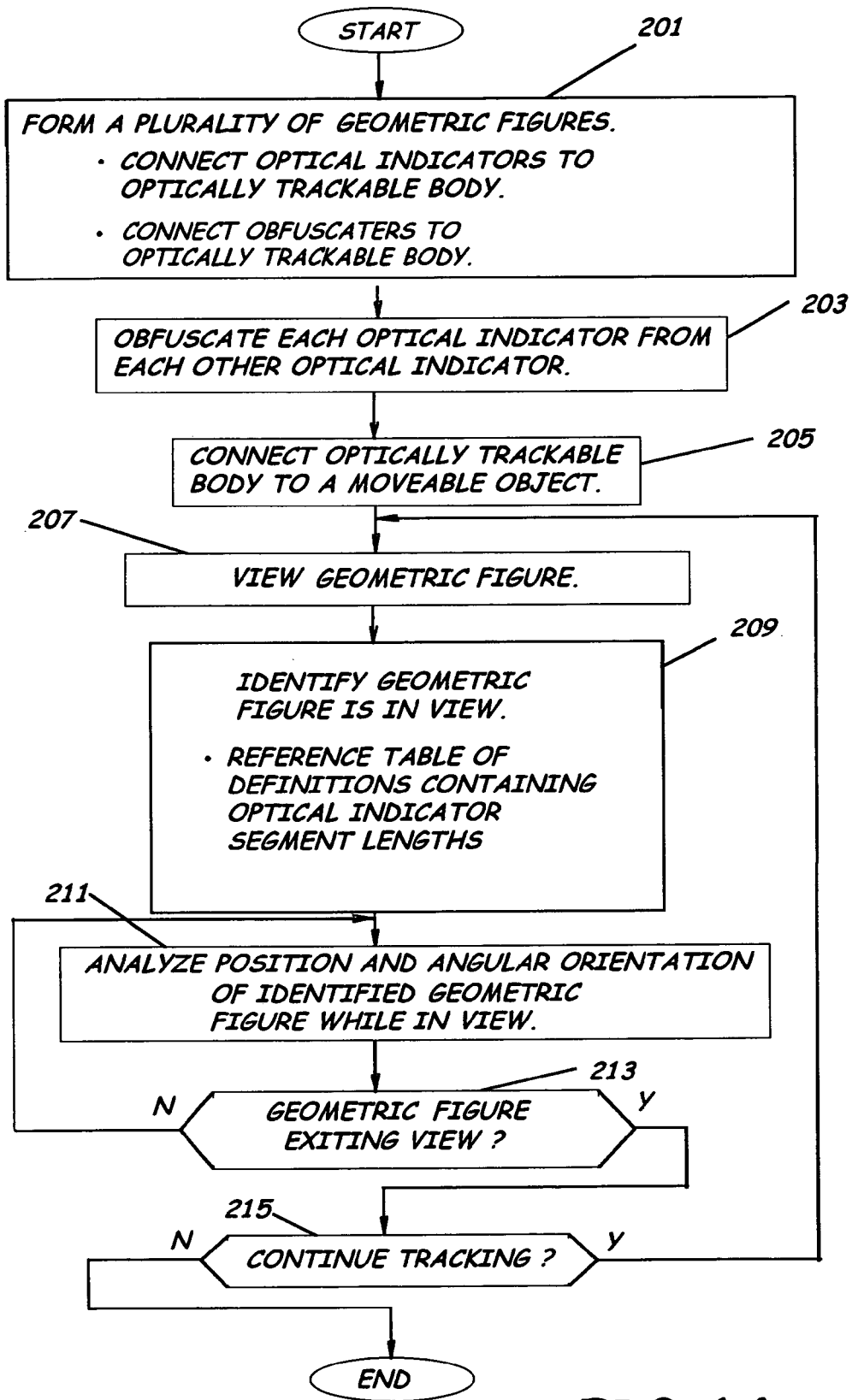
FIG. 14 is flowchart of a method for tracking position and orientation of a movable object according to an embodiment of the present invention.

As perhaps best shown in FIGS. 6 and 13, the proximal body end portion of the optically trackable body 23 can further include a proximal body end mounting extension 61 connected to and preferably integral with the proximal body end portion 41 of the optically trackable body 23. The proximal body end mounting extension 61 can generally extend perpendicular to and outwardly from the longitudinal axis L (FIG. 5) of the optically trackable body 23. The proximal body end mounting extension 61 can have a substantially flat planer proximal end surface 63 adapted to interface with a surface of the movable object O or a surface of a movable object mounting interface of an intermediate mount, such as movable object mount 65 (FIG. 2) or movable object mount 67 (FIG. 3). The proximal body end mounting extension 61, for example, advantageously, can include a proximal body end portion support flange 69 positioned within and extending longitudinally from outer surface peripheries of the proximal end surface 63 of the proximal body end 41 of the optically trackable body 23. The proximal body end portion support flange 69, preferably integral with the proximal body end 41 of the optically trackable body 23, forms a proximal end surface recess 70 which can slidably receive at least portions of either of the movable object mounts 65, 67 (FIGS. 2-3).

As shown in FIGS. 6 and 13, the optically trackable body 23 can also include an interior mount recess 71 inwardly extending from the proximal body end portion 41 into the medial body portion 45. The interior mount recess 71 can be used to connect the optically trackable body 23 to the movable object O (FIGS. 2-3). The interior mount recess 71 is adapted to slidably receive at least portions of a mounting connector, such as, for example, movable object mounting connector 73 (FIG. 2) or movable object connector 75 of movable object mount 67 (FIG. 3).

In order to ensure the mounting connector 73 or 75 is properly inserted and radially aligned with the interior mount recess 71 of the optically trackable body 23, the optically trackable body 23 can also include at least one mounting connector retention member, preferably in the form of a collapsible mounting connector retention lock member 81. At least portions of the collapsible mounting connector retention lock member 81 are housed in a mounting connector retention recess 83 which is positioned substantially normal to the interior mount recess 71 and provided to house the at least portions of the collapsible mounting connector retention lock member 81. The mounting connector retention recess 83 can be formed in either the medial body portion 45 of the optically trackable body 23 or a medial portion of the proximal body end mounting extension 61, depending upon the selected configuration. The mounting connector retention recess 83 can extend between outer surface portions of either the medial body portion 45 or the proximal body end mounting extension 61, respectively, and inner surface portions of the interior mount recess 71, to releasably fixedly retain the mounting connector 73, 75 (FIGS. 2, 3), within the interior mount recess 71, when so positioned. If a second mounting connector retention lock member 81 (not shown) is used, it is preferably positioned opposite the first mounting connector retention lock member 81 in a corresponding recess. Advantageously, the various mounting connectors including mounting connectors 73, 75, allow the optically trackable body 23 to be easily removable and interchangeable with other trackers 21, enabling a variety of different applications. Additionally, advantageously mounting connector 75 (FIG. 3) can include an interior mounting connector recess 77 which can receive mounting connector 75 (FIG. 2), such that the two mounting connectors 73, 75, can be synergistically implemented together (described later).

In an embodiment of the present invention, the collapsible mounting connector retention lock member 81 can include a preferably spring loaded plunger 85 and a fastener in the form of a set screw 87 used to adjust tension or bias on the spring loaded plunger 85, defining a quick release. The spring loaded plunger 85 and set screw 87 are adapted to radially compel the proximal body end mounting extension 61 of the optically trackable body 23 in a predetermined position with respect to the movable object O or the movable object mount 65, 67, to thereby prevent the optically trackable body 23 from being mounted to either the movable object O or the movable object mount 65, 67, in an incorrect longitudinal orientation. Note, movable object mount 67 also can help prevent mounting the optically trackable body 23 in an incorrect angular orientation (described later). Note also, advantageously, the spring loaded plunger 85 can negate the requirement for the use of tools to accurately and repeatably position the optically trackable body 23 in the correct juxtaposition with the movable object O to be tracked, and thus, correspondingly can allow for the optically trackable body 23 to be easily and durably manufactured with high tolerances.

The plunger 85 of the collapsible mounting connector retention lock member 81 is adapted to extend through inner surface portions of the interior mount recess 71 when the mounting connector 73, 75, is substantially extended inward within the interior mount recess 71 defining at least a partially collapsed and inwardly biased lock position and adapted to collapse outward responsive to an outward pressure from the mounting connector 73, 75, when the mounting connector 73, 75, is partially retracted outward from within the interior mount recess 71 defining a collapsed and unlocked position. The plunger 85 of the collapsible mounting connector retention lock member 81 is further adapted to extend inward through the inner surface portions of the interior mount recess 71 when the mounting connector 73, 75, is substantially retracted outward from within the interior mount recess 71 defining a non-collapsed and inwardly biased position. The set screw 87 should be set to provide sufficient spring tension such that, when used by an operator, the optically trackable body 23 is maintained connected to the movable object O, and such that application of an extraction force by the operator will result in compression of the spring loaded plunger 85 and release of the optically trackable body 23 from the movable object O or movable object mount 65, 67.

As perhaps best shown in FIG. 2, the mounting connector 73 can include a notch or recess, such as either a radial recess (not shown) or an annular mounting connector recess 91, which can be adapted to receive the plunger 85 of the collapsible mounting connector retention lock member 81 to releasably fixedly retain the mounting connector 73 within the interior mount recess 71, when so positioned. When the recess is annular or otherwise not radially restrictive to the plunger 85, a radial mount alignment key 93, typically connected to the movable object mount 65, but alternatively connected to the movable object O, can be used to prevent annular rotation of the optically trackable body 23 with respect to the movable object O. The mount alignment key 93 is adapted to radially compel the proximal body end portion 41 (proximal body end mount the extension 61) of the optically trackable body 23 in a predetermined position with respect to the movable object O and the movable object mount 65, 67, if so implemented, to thereby prevent the optically trackable body 23 from being mounted via the movable object O via the movable object mount 65, 67, in an incorrect angular orientation. Correspondingly, the proximal body end portion 41 of the optically trackable body 23 can also include at least one longitudinal body alignment recess 97 (FIG. 7). The longitudinal body alignment recess 97 is positioned parallel to and spaced radially apart from the longitudinal axis L (FIG. 5) of the optically trackable body 23 to slidably receive at least portions of the mount alignment key 93.

If the selected mounting configuration of the tracker 21 includes implementation of the mounting connector 73 within the interior mounting connector recess 77 in the mounting connector 75 of the movable object mount 67, a longitudinal mount alignment key recess 101 (FIG. 3) can be positioned in a radial extension 103 extending radially and outwardly from proximal end portions of the mounting connector 75. Further, the mounting connector 75 of the movable object mount 67 can also include a notch or recess, such as radial recess 105 positioned in a medial body portion of the mounting connector 75. The recess 105 can be adapted to receive at least portions of the plunger 85 of the collapsible mounting connector retention lock member 81 to releasably fixedly retain the mounting connector 75 within the interior mount recess 71, when so positioned. The plunger 85 can be positioned with sufficient spring tension using set screw 87 to engage the annular recess 91 of the mounting connector 73 through a radial recess 105 (FIG. 3). In this configuration, the longitudinal mount alignment key recess 101 can negate any requirement for longitudinal body alignment recess 97 (FIG. 7) in the proximal body end portion 41 of the optically trackable body 23.

As perhaps best shown in FIG. 3, the movable object mount 67 can be used as a stand-alone interface with the movable object O or an intermediate mount positioned therebetween (not shown). The radial extension 103 can include at least one but preferably a pair of longitudinal fastener apertures 107 positioned spaced apart on opposite sides (radial positions) of the mounting connector 75. The longitudinal fastener apertures 107 are adapted to receive fasteners (not shown) known and understood by those skilled in the art to fixedly connect the movable object mount 67 to the movable object O or movable object mount 65. Advantageously, in conjunction with plunger 85 and radial recess 105, such implementation allows the optically trackable body 23 to be quickly, and preferably without tools, connected and disconnected from the movable object O.

As perhaps best shown in FIG. 1 and as stated above, the system 20 also includes an apparatus to track a trackable body or camera subsystem 31. Optical tracking apparatus or camera systems are well-known to those skilled in the art. For example, one such system found to be effective with use of the tracker 21 is a camera or opti-electrical motion measurement system, known as the Polaris®, by Northern Digital Inc., Ontario Canada. The illustrated apparatus to track a trackable body or camera subsystem 31 typically includes an optical detector 33 and a determiner 35. The optical detector 33 has an optical detector body 111 positioned separate and spaced apart from the optically trackable body 23 at a predetermined three-dimensional sensor reference location. The optical detector 33 preferably includes a pair of separate and spaced apart optical receivers 113, 115, connected to the optical detector 33 body, each having a field of view V and being adapted to receive optical energy emitted or reflected by each of the plurality of optical retro-reflective spheres 25 when positioned in the field of view typically (centered about the optical receiver pointing angle). The optical receivers 113, 115, detect the three-dimensional sphere 25 position of each of the plurality of retro-reflective spheres 25 when positioned simultaneously within the field of view of both of the optical receivers 113, 115 to produce a plurality of position signals representing the position of such three-dimensional retro-reflective spheres 25. Each of the optical receivers 113, 115, can include a photo-sensitive array (not shown) such as a two-dimensional array charge coupled device CCD sensor or other similar device, defining a photosensor, to detect optical energy radiated from the retro-reflective spheres 25 when positioned in the field of view of the optical receiver 113, 115. The photosensor provides electrical signals representative of positional information of the retro-reflective spheres 25. Each of the optical receivers 113, 115, also generally include a lens (not shown) for focusing the optical energy from the retro-reflective spheres 25 on the photosensor.

Where the plurality of indicators are in the form of optical retro-reflective spheres 25, the optical detector 33 can include a pair of infrared illuminators, preferably in the form of a pair of directional infrared illuminator (arrays) 117, 119. The first illuminator 117 is positioned in a surrounding relationship adjacent optical receiver 113 and the second illuminator 119 is positioned adjacent the other optical receiver 115 to selectively illuminate each of the plurality of optical retro-reflective spheres 25 when positioned in the field of view of the respective adjacent optical receiver 113, 115. This provides the requisite optical energy necessary to view the optical retro-reflective spheres 25 within the field of view of the respective adjacent optical receiver 113, 115.

The determiner 35 is in communication with the optical detector 33 and is responsive to the plurality of position signals produced by the optical detector 33 to determine the three-dimensional retro-reflective sphere 25 position of each of the plurality of retro-reflective spheres 25 when positioned simultaneously within the field of view of both of the optical receivers (113, 115) of the optical detector 33. The determiner 35 can include a processor 121 to analyze the two-dimensional position of each sphere 25 in the field of view of both receivers 113, 115, with respect to the position on the photosensor, to determine the three-dimensional location of each sphere 25 simultaneously in the field of view of the receivers 113, 115. The determiner 35 can also include a memory 123 accessible by the processor 121 to store a table of definitions containing the segment lengths S between each pair of the plurality of optical retro-reflective spheres 25. Note, although the illustrated embodiment shows the detector 33 and the determiner 35 as a separate unit, typically in a passive tracking system, such as that described below, the detector 33 and determiner 35 form a single unit. For simplicity, however, they are illustrated as separate units.

Responsive to the segment lengths S and the three-dimensional location of at least three retro-reflective spheres 25 simultaneously in the field of view of both optical receivers 113, 115, the determiner 35 can determine which of the plurality of geometric figures F (FIG. 2) is in view of the optical receivers 113, 115. Once the particular geometric figure F is identified, the determiner 35, by determining the current orientation of the particular geometric figure F, can then further determine the three-dimensional position and the orientation of the optically trackable body 23 of tracker 21, and thus, the movable object O. In an embodiment of the present invention, the plurality of retro-reflective spheres 25 are assigned three-dimensional coordinate positions with respect to an origin (not shown) of a coordinate system assigned to the tracker 21 to provide a reference to the origin and a linear direction of each axes (not shown) of the assigned coordinate system of the tracker 21. The linear direction of each axes of the assigned coordinate system of the tracker coincide with an orientation of each geometric figure F, and thus, can define the orientation of the tracker 21. Note, although in this preferred embodiment of the present invention, the linear direction of the axes of the coordinate system assigned to the tracker 21 are utilized to define the orientation of the tracker 21, other methodologies of defining orientation, known by those skilled in the art, are within the scope of the present invention. For example, orientation could be defined as the longitudinal, lateral, or some other real or user-defined axes of the tracker 21.

As perhaps best shown in FIGS. 5, 7, and 8, advantageously, the plurality of retro-reflective spheres 25 and obfuscating flanges 51, 55, 57, of the tracker 21 are synergistically positioned to enhance optical tracking of the tracker 21, and thus, the movable object O, with few exceptions, at substantially any given orientation of the tracker 21 when viewed by the apparatus or camera subsystem 31 (FIG. 1). The few exceptions that are inherent in various embodiments of the present invention are, generally, not problematic. For example, in the preferred embodiment of the present invention, the optical detector 33 of the apparatus or camera subsystem 31 typically will not maintain a tracking solution on the optically trackable body 23 if the longitudinal axis L is aligned with the optical detector 33 such that the axis L extends through the optical center of the optical detector 33, shown at 125 in FIG. 1 for illustrative purposes only, a position approximately centered between the optical receivers 113, 115, of the optical detector 33 in the illustrated embodiment of the present invention. As perhaps best conceptually shown in FIG. 8, if the distal body end portion 43 is "pointed" towards the optical detector 33, a small circular blind spot (not shown) may be created in which the optical receivers 113, 115, of the optical detector 33 may not simultaneously view at least three of the same spheres 25 of the plurality of spheres 25, due to their offset viewing angles. Also, as perhaps best conceptually shown in FIG. 7, if the proximal body end portion 41 is "pointed" toward the optical detector 33, a large circular blind spot (not shown) may be created in which the optical receivers 113, 115, of the optical detector 33 may not simultaneously view at least three of the same spheres 25 of the plurality of spheres 25 (along their active portions). Additionally, the movable object O would tend to block the view of the optical detector 33. Though the large blind spot may appear problematic at first blush, it is generally not problematic as a movable object O, such as the illustrated ultrasound wand, would be in an inoperative state if pointed directly at the optical detector 33. A tracking solution would be reacquired once the ultrasound wand is again positioned in an operative state.

Methods for tracking a position and an orientation of a movable object O are also advantageously provided. For example, as perhaps best shown in FIG. 14, in an embodiment of the present invention, a method for tracking a position and an orientation of a movable object O includes the steps of (block 201) connecting a plurality of retro-reflective spheres 25 to an optically trackable body 23 to form a plurality of preferably dissimilar geometric figures F (FIG. 2). Though in the illustrated embodiment the obfuscating flanges 51, 55, 57 (FIG. 5) are unitary with the optically trackable body 23, in an alternative embodiment, if not already either part of the optically trackable body 23 or pre-connected to said body, the obfuscating flanges can be connected. Regardless, the optically trackable body 23 is provided a plurality of obfuscating flanges 51, 55, 57 (FIG. 5), sized and positioned to obfuscate or optically separate each of the plurality of retro-reflective spheres 25 from each other (block 203) to prevent each of the plurality of retro-reflective spheres 25 from becoming optically coincident with another one of the plurality of retro-reflective spheres 25 when viewed by an observer such as, for example, either optical receiver 113, 115, along a preselected viewing path, such as, for example, paths P1-3 (FIG. 5).

The optically trackable body 23 can be connected (block 205) to a movable object O, illustrated, for example, as an ultrasound wand (FIGS. 1-2). A connection can be provided by means known to those skilled in the art to include various movable object mounts, such as movable object mount 65, 67. The ultrasound wand includes an ultrasonic sensor (not shown) adapted to locate a three-dimensional position of an area of interest of a target or tumor (not shown) with respect to a position of the ultrasound wand.

An optical detector 33 (FIG. 1) can be used to view the spheres 25 positioned in its field of view, and thus, view (block 207) at least one of the plurality of geometric figures F (FIG. 2). A determiner 35 can then be used to identify (block 209) which one of the plurality of geometric figures F is positioned in the field of view of the optical detector 33. A lookup table containing various segment lengths between pair combinations of the retro-reflective spheres 25, or similar collection of data, can be used.

The determiner 35 can analyze (block 211) the position and orientation of the identified geometric figure F in the field of view of the optical detector 33 which can then be used to determine the position and orientation of the ultrasound wand. Specifically, responsive to position signals produced by the optical detector 33 regarding the retro-reflective spheres 25 in the field of view of the optical detector 33 and segment lengths S previously stored of a table of definitions stored in a memory 123 of the determiner 35, the determiner 35 can determine the three-dimensional position and the orientation (viewing angle) of the ultrasound wand.

By continuously analyzing the position and orientation of the geometric figures F, the position and orientation of the ultrasound wand can be continuously re-determined while the geometric figures F remains in the field of view of the optical detector 33. The position and orientation of the ultrasound wand can be continuously tracked through various rotations of the ultrasound wand by obfuscating a first of the plurality of retro-reflective spheres 25 as it leaves the field of view of the optical detector 33 to prevent the first of the plurality of retro-reflective spheres 25 from becoming optically coincident with a second of the plurality of retro-reflective spheres 25. This allows the determiner 35, upon determining one of the plurality of geometric figures F is exiting view (block 213), to thereby replace the one of the plurality of geometric figures F positioned in the field of view of the optical detector 33 with another one of the plurality of geometric figures F positioned in the field of view of the optical detector 33. This second of the plurality of figures F can then continuously be tracked (block 215) until replaced with a third of the plurality of figures F to provide continuous tracking.

Advantageously, in this illustrative embodiment of the present invention, because the ultrasound wand can relate the position of the target or tumor to its own position, the determiner 35 can thereby determine the three-dimensional position of various areas of interest of the target or tumor. Correspondingly, by manipulating and tracking the viewing angle of the ultrasound wand and examining the tumor through multiple viewing angles, an operator can thereby further ascertain the orientation of the target or tumor.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims. For example, embodiments of the present invention were described particularly in the context of an ultrasound wand. Other suitable movable objects, such as for example robot arms, and medical tools, such as for example medical catheters, are contemplated. Additionally, embodiments of the present invention were particularly described with respect to retro-reflective spheres, however, other passive or active optical indicators are within the scope of the present invention. Further, embodiments of the present invention were described having obfuscating flanges positioned to separate each of the plurality of indicators or retro-reflective spheres. Alternative embodiments can include indicators or spheres where a portion of them are not optically separated by obfuscators. These unseparated indicators or spheres, however, are more likely to become optically coincident when being viewed. Embodiments of the present invention were described to incorporate the Polaris® measurement system. Other systems or apparatus for tracking a trackable body are within the scope of the present invention.

That claimed is:

1. A system for tracking a three-dimensional position and an orientation of a movable object, the system comprising:
   a tracker comprising:
      a plurality of separate and spaced apart optical retro-reflective spheres having a preselected segment length between each pair combination of the plurality of optical retro-reflective spheres, a plurality of combinations of at least three of the plurality of optical retro-reflective spheres defining a plurality of geometric figures, each of the plurality of retro-reflective spheres adapted to be optically tracked over a subset of possible movable object orientations to provide three-dimensional positional data and orientation data of the movable object, and
      an optically trackable body having the plurality of optical retro-reflective spheres mounted thereto and having a proximal body end portion, a distal body end portion, a medial body portion connected to and extending between the proximal body end portion and the distal body end portion, a longitudinal axis, and separating means for optically separating each of the plurality of optical retro-reflective spheres from each other to prevent each of the plurality of retro-reflective spheres from becoming optically coincident with another one of the plurality of retro-reflective spheres when viewed along a collinear viewing path extending directly through either adjacent pair of the plurality of retro-reflective spheres to enhance optical detection of the plurality of retro-reflective spheres to thereby enhance determination of the positional location and orientation of the movable object; and an apparatus to track a trackable body, the apparatus comprising:

an optical detector having an optical detector body adapted to be positioned separate and spaced apart from the optically trackable body at a three-dimensional optical detector reference location, and including a pair of separate and spaced apart optical receivers connected to the optical detector body, each having a field of view and being adapted to receive optical energy reflected by each of the plurality of optical retro-reflective spheres when positioned in the field of view to thereby detect the three-dimensional sphere position of each of the plurality of retro-reflective spheres when positioned simultaneously within the field of view of both of the optical receivers to produce a plurality of position signals representing such three-dimensional sphere positions, and a pair of infrared illuminators, a first illuminator positioned adjacent one of the pair of separate and spaced apart optical receivers and a second illuminator positioned adjacent the other of the pair of separate and spaced apart optical receivers to selectively illuminate each of the plurality of optical retro-reflective spheres when positioned in the field of view of the respective adjacent optical receiver to thereby energize the optical retro-reflective spheres within the field of view of the respective adjacent optical receiver, and a determiner in communication with the optical detector and responsive to the plurality of position signals produced by the optical detector to determine the three-dimensional sphere position of each of the plurality of retro-reflective spheres when positioned simultaneously within the field of view of both of the optical receivers of the optical detector and having a memory associated therewith to store a table of definitions containing the segment lengths between each of the plurality of optical retro-reflective spheres to determine, responsive to the segment lengths, which of the plurality of geometric figures is in view of the optical receivers, when so positioned, to thereby determine the three-dimensional position and the orientation of the movable object.

2. A system as defined in claim 1, wherein the separating means includes a plurality of medial body portion obfuscating flanges sized and positioned substantially parallel to and spaced apart from the longitudinal axis of the medial body portion of the optically trackable body to optically separate each sphere of the plurality of optical retro-reflective spheres mounted to the medial body portion of the optically trackable body from each adjacent sphere of the plurality of optical retro-reflective spheres also mounted to the medial body portion of the optically trackable body to prevent each sphere of the plurality of retro-reflective spheres mounted to the medial body portion of the optically trackable body from becoming optically coincident with each adjacent sphere of the plurality of optical retro-reflective spheres also mounted to the medial body portion of the optically trackable body, when viewed along the collinear viewing path of either of the pair of optical receivers.

3. A system as defined in claim 1, wherein the separating means includes a medial body portion obfuscating flange positioned substantially axially parallel with the longitudinal axis of the medial body portion of the optically trackable body and positioned and sized to optically separate each sphere of the plurality of optical retro-reflective spheres mounted to the distal body end portion of the optically trackable body from each sphere of the plurality of optical retro-reflective spheres mounted to the medial body portion of the optically trackable body to prevent each sphere of the plurality of retro-reflective spheres mounted to the distal body portion of the optically trackable body from becoming optically coincident with each other sphere of the plurality of optical retro-reflective spheres mounted to the medial body portion of the optically trackable body, when viewed along the collinear viewing path of either of the pair of optical receivers.

4. A system as defined in claim 1, wherein the distal body end portion of the optically trackable body has a pair of adjacent optical retro-reflective spheres mounted thereto, and wherein the separating means includes a distal body end portion obfuscating flange positioned substantially axially perpendicular to the longitudinal axis of the medial body portion of the optically trackable body and positioned and sized to optically separate a first sphere of the pair of optical retro-reflective spheres mounted to the distal body end portion of the optically trackable body from a second sphere of the pair of optical retro-reflective spheres mounted to the distal body portion of the optically trackable body to prevent the first sphere of the pair of adjacent optical retro-reflective spheres mounted to the distal body end portion of the optically trackable body from becoming optically coincident with the second sphere of the pair of optical retro-reflective spheres mounted to the distal body end portion of the optically trackable body, when viewed along the collinear viewing path of either of the pair of optical receivers.

5. A system as defined in claim 1, wherein each sphere in the plurality of optical retro-reflective spheres is positioned to form at least two of the plurality of geometric figures to reduce a selected number of spheres required to determine the positional location and orientation of the movable object to thereby reduce overall size and complexity of the optically trackable body.

6. A system as defined in claim 1, further comprising a mounting connector adapted to connect the optically trackable body to the movable object, and wherein the optically trackable body further includes an interior mount recess inwardly extending from the proximal body end portion into the medial body portion and adapted to slidably receive at least portions of the mounting connector.

7. A system as defined in claim 6, wherein the mounting connector includes an annular mounting connector recess adapted to receive the mounting connector within the interior mount recess when so inserted, and wherein the medial body portion of the optically trackable body further includes a mounting connector retention recess extending between outer surface portions of the medial body portion and inner surface portions of the interior mount recess and positioned substantially normal to the interior mount recess to house at least portions of a mounting connector retention lock member.

8. A system as defined in claim 6, wherein the medial body portion of the optically trackable body further includes a mounting connector retention recess extending between outer surface portions of the medial body portion and inner surface portions of the interior mount recess and positioned substantially normal to the interior mount recess, and a collapsible mounting connector retention lock member housed at least partially within the mounting connector retention recess and adapted to extend through inner surface portions of the interior mount recess when the mounting connector is substantially extended inward within the interior mount recess defining at least a partially-collapsed and inwardly biased lock position, adapted to collapse outward responsive to an outward pressure from the mounting connector when the mounting connector is partially retracted outward from within the interior mount recess defining a collapsed and an unlocked position, and adapted to extend inward through the inner surface portions of the interior mount recess when the mounting connector is substantially retracted outward from within the interior mount recess defining a non-collapsed and inwardly biased unlocked position.

9. A system as defined in claim 1, wherein the proximal body end portion of the optically trackable body further includes a proximal body end mounting extension connected to and integral with the proximal body end portion of the body, extending substantially perpendicular to and outwardly from the longitudinal axis of the optically trackable body, and having a substantially flat planer proximal surface adapted to interface with a surface of at least one of the movable object and a movable object mount.

10. A system as defined in claim 9, wherein the proximal body end mounting extension includes at least one longitudinal recess parallel to and spaced radially apart from the longitudinal axis of the optically trackable body and adapted to receive at least portions of at least one of the movable object mount and a mount alignment key and adapted to angularly compel the proximal body end mounting extension of the optically trackable body in a predetermined position with respect to at least one of the movable object and the movable object mount to thereby prevent the optically trackable body from being mounted to the at least one of the movable object and the movable object mount in an incorrect orientation.

11. A tracker comprising:
a plurality of separate and spaced apart indicators having a preselected segment length between each pair combination of the plurality of indicators, a plurality of combinations of at least three of the plurality of indicators to form a plurality of geometric figures, each of the plurality of indicators adapted to be optically tracked over a subset of possible movable object orientations to provide three-dimensional positional data and orientation data of the movable object; and
an optically trackable body having the plurality of indicators mounted thereto and having a proximal body end portion, a distal body end portion, a medial body portion connected to and extending between the proximal body end portion and the distal body end portion, a longitudinal axis, and a plurality of obfuscating flanges sized and positioned to optically separate each of the plurality of indicators from each other to prevent each of the plurality of indicators from becoming optically coincident with another one of the plurality of indicators when viewed along a plurality of viewing paths extending directly through each pair combination of the plurality of indicators to enhance optical detection of the plurality of indicators.

12. A tracker as defined in claim 11, wherein the plurality of obfuscating flanges includes a plurality of medial body portion obfuscating flanges sized and positioned substantially parallel to extending outwardly from the longitudinal axis of the medial body portion of the optically trackable body to optically separate each indicator of the plurality of indicators mounted to the medial body portion of the optically trackable body from each adjacent indicator of the plurality of indicators also mounted to the medial body portion of the optically trackable body to prevent each indicator of the plurality of indicators mounted to the medial body portion of the optically trackable body from becoming optically coincident with each adjacent indicator of the plurality of indicators also mounted to the medial body portion of the optically trackable body, when viewed along either of the plurality of viewing paths extending directly through each adjacent pair of the plurality of indicators mounted to the medial body portion of the optically trackable body.

13. A tracker as defined in claim 11, wherein the plurality of obfuscating flanges includes a medial body portion obfuscating flange positioned substantially axially parallel with the longitudinal axis of the medial body portion of the optically trackable body and positioned and sized to optically separate each indicator of the plurality of indicators mounted to the distal body end portion of the optically trackable body from each indicator of the plurality of indicators mounted to the medial body portion of the optically trackable body to prevent each indicator of the plurality of indicators mounted to the distal body portion of the optically trackable body from becoming optically coincident with each other indicator of the plurality of indicators mounted to the medial body portion of the optically trackable body, when viewed along either of the plurality of viewing paths extending directly through each indicator of the plurality of indicators mounted to the distal body portion of the optically trackable body and either indicator of the plurality of indicators mounted to the medial body portion of the optically trackable body.

14. A tracker as defined in claim 11, wherein the distal body end portion of the optically trackable body has a pair of adjacent indicators mounted thereto, and wherein the plurality of obfuscating flanges includes a distal body end portion obfuscating flange positioned substantially axially perpendicular to the longitudinal axis of the medial body portion of the optically trackable body and positioned and sized to optically separate a first indicator of the pair of indicators mounted to the distal body end portion of the optically trackable body from a second indicator of the pair of indicators mounted to the distal body portion of the optically trackable body to prevent the first indicator of the pair of adjacent indicators mounted to the distal body end portion of the optically trackable body from becoming optically coincident with the second indicator of the pair of indicators mounted to the distal body end portion of the optically trackable body, when viewed along either of the plurality of viewing paths extending directly through the first and second indicators of the pair of adjacent indicators mounted to the distal body end portion of the optically trackable body.

15. A tracker as defined in claim 11, wherein each indicator in the plurality of indicators is positioned to form at least two of the plurality of geometric figures to reduce a selected number of indicators required to determine the positional location and orientation of the movable object to thereby reduce overall size and complexity of the optically trackable body.

16. A tracker as defined in claim 11, further comprising a mounting connector adapted to connect the optically trackable body to the movable object, and wherein the optically trackable body further includes an interior mount recess inwardly extending from the proximal body end portion into the medial body portion and adapted to slidably receive at least portions of the mounting connector, when so positioned.

17. A tracker as defined in claim 16, wherein the medial body portion of the optically trackable body further includes a mounting connector retention recess extending between outer surface portions of the medial body portion and inner surface portions of the interior mount recess and positioned substantially normal to the interior mount recess to house at least portions of a mounting connector retention member, and wherein the mounting connector includes an annular mounting connector recess adapted to receive at least portions of the mounting connector retention member to fixedly retain the mounting connector within the interior mount recess when so positioned.

18. A tracker as defined in claim 16, wherein the medial body portion of the optically trackable body further includes a mounting connector retention recess extending between outer surface portions of the medial body portion and inner surface portions of the interior mount recess and positioned substantially normal to the interior mount recess, and a collapsible mounting connector retention lock member housed at least partially within the mounting connector retention recess and adapted to extend through inner surface portions of the interior mount recess when the mounting connector is substantially extended inward within the interior mount recess defining at least a partially-collapsed and inwardly biased lock position, adapted to collapse outward responsive to an outward pressure from the mounting connector when the mounting connector is partially retracted outward from within the interior mount recess defining a collapsed and unlocked position, and adapted to extend inward through the inner surface portions of the interior mount recess when the mounting connector is substantially retracted outward from within the interior mount recess defining a non-collapsed and inwardly biased unlocked position.

19. A tracker as defined in claim 11, wherein the optically trackable body further includes a proximal body end mounting extension connected to and integral with the proximal body end portion of the body, substantially extending perpendicular to and outwardly from the longitudinal axis of the optically trackable body, and having a substantially flat planer proximal surface adapted to interface with a surface of at least one of the movable object and a movable object mount.

20. A tracker as defined in claim 19, wherein the proximal body end mounting extension includes at least one longitudinal recess parallel to and spaced radially apart from the longitudinal axis of the optically trackable body and adapted to receive at least portions of at least one of the movable object mount and a mount alignment key adapted to angularly compel the proximal body end mounting extension of the optically trackable body in a predetermined position with respect to at least one of the movable object and the movable object mount to thereby prevent the optically trackable body from being mounted to the at least one of the movable object and the movable object mount in an incorrect orientation.

21. A tracker to provide three-dimensional positional data and orientation data about a positional location and orientation of a movable medical tool, the tracker comprising:
an optically trackable body adapted to connect to the movable medical tool, having a plurality of indicators mounted thereto and having a proximal body end portion, a distal body end portion, a medial body portion connected to and extending between the proximal body end portion and the distal body end portion, a body longitudinal axis, and at least one obfuscating flange sized and positioned to optically separate a first of the plurality of optical indicators from a second of the plurality of indicators to prevent the first of the plurality of indicators from becoming optically coincident with the second of the plurality of indicators when viewed along a viewing path extending directly through the first and second indicators to thereby enhance optical detection of the plurality of indicators.

22. A tracker as defined in claim 21, wherein the at least one obfuscating flange includes a plurality of longitudinal medial body portion obfuscating flanges sized and positioned substantially parallel to and spaced apart from the longitudinal axis of the medial body portion of the optically trackable body to optically separate each indicator of the plurality of indicators mounted to the medial body portion of the optically trackable body from each adjacent indicator of the plurality of indicators also mounted to the medial body portion of the optically trackable body to prevent each indicator of the plurality of indicators mounted to the medial body portion of the optically trackable body from becoming optically coincident with each adjacent indicator of the plurality of indicators also mounted to the medial body portion of the optically trackable body, when viewed along either of a plurality of viewing paths extending directly through each adjacent pair of the plurality of indicators mounted to the medial body portion of the optically trackable body.

23. A tracker as defined in claim 22, wherein the at least one obfuscating flange includes a medial body portion obfuscating flange positioned substantially axially parallel with the longitudinal axis of the medial body portion of the optically trackable body and positioned and sized to optically separate each indicator of the plurality of indicators mounted to the distal body end portion of the optically trackable body from each indicator of the plurality of indicators mounted to the medial body portion of the optically trackable body to prevent each indicator of the plurality of indicators mounted to the distal body portion of the optically trackable body from becoming optically coincident with each indicator of the plurality of indicators mounted to the medial body portion of the optically trackable body, when viewed along either of a plurality of viewing paths extending directly through each indicator of the plurality of indicators mounted to the distal body portion of the optically trackable body and either indicator of the plurality of indicators mounted to the medial body portion of the optically trackable body.

24. A tracker as defined in claim 22, wherein the distal body end portion of the optically trackable body has a pair of adjacent indicators mounted thereto, and wherein the plurality of obfuscating flanges includes a distal body end portion obfuscating flange positioned substantially axially perpendicular to the longitudinal axis of the medial body portion of the optically trackable body and positioned and sized to optically separate a first indicator of the pair of indicators mounted to the distal body end portion of the optically trackable body from a second indicator of the pair of indicators mounted to the distal body portion of the optically trackable body to prevent the first indicator of the pair of adjacent indicators mounted to the distal body end portion of the optically trackable body from becoming optically coincident with the second indicator of the pair of indicators mounted to the distal body end portion of the optically trackable body, when viewed along a viewing path extending directly through the first and second indicators of the pair of adjacent indicators mounted to the distal body end portion of the optically trackable body.

25. A tracker as defined in claim 21, further comprising a mounting connector adapted to connect the optically trackable body to the movable medical tool, and wherein the optically trackable body further includes an interior mount recess inwardly extending from the proximal body end portion into the medial body portion and adapted to slidably receive at least portions of the mounting connector, when so positioned.

26. A tracker as defined in claim 25, wherein the medial body portion of the optically trackable body further includes a mounting connector retention recess extending between outer surface portions of the medial body portion and inner surface portions of the interior mount recess and positioned substantially normal to the interior mount recess to house at least portions of a mounting connector retention member, and wherein the mounting connector includes a radial mounting connector recess extending from outer surface portions of the mounting connector radially within the mounting connector and adapted to receive at least portions of the mounting connector retention member to fixedly retain the mounting connector within the interior mount recess when so positioned.

27. A tracker as defined in claim 21, wherein the proximal body end portion of the optically trackable body further includes a proximal body end mounting extension connected to and integral with the proximal body end portion of the body, extending substantially perpendicular to and outwardly from the longitudinal axis of the optically trackable body and having a substantially flat planer proximal surface adapted to interface with a surface of at least one of the movable medical tool and a movable medical tool mount.

28. A tracker as defined in claim 27, wherein the proximal body end mounting extension includes at least one longitudinal recess parallel to and spaced radially apart from the longitudinal axis of the optically trackable body and adapted to receive at least portions of at least one of the movable medical tool mount and a mount alignment key adapted to axially compel the proximal body end mounting extension of the optically trackable body in a predetermined axial position with respect to at least one of the movable medical tool and the movable medical tool mount to thereby prevent the optically trackable body from being mounted to the at least one of the movable medical tool and the movable medical tool mount in an incorrect orientation.

29. A tracker as defined in claim 25, wherein the proximal body end portion of the optically trackable body further includes a proximal body end mounting extension connected to and integral with the proximal body end portion of the body, extending substantially perpendicular to and extending outwardly from the longitudinal axis of the optically trackable body, and having a substantially flat planer proximal surface adapted to interface with a surface of at least one of the movable medical tool and a movable medical tool mount, and a mounting connector retention recess extending between outer surface portions of the proximal body end mounting extension and inner surface portions of the interior mount recess and positioned substantially normal to the interior mount recess to house at least portions of a mounting connector retention member, and wherein the mounting connector includes a radial mounting connector recess extending from outer surface portions of the mounting connector radially within the mounting connector and adapted to receive at least portions of the mounting connector retention member to fixedly retain the mounting connector within the interior mount recess, when so positioned.

30. A tracker as defined in claim 21, further comprising a plurality of separate and spaced apart indicator mounts having a dissimilar, preselected length between each pair combination of the plurality of mounts and extending radially outward from the body longitudinal axis about a circumference of the optically trackable body and adapted to mount the plurality of indicators to the optically trackable body, and wherein the plurality of indicators provide three-dimensional positional data and orientation data of the optically trackable body for substantially all possible movable object orientations.

31. A method for tracking a position and an orientation of a movable object, comprising the steps of:
 (a) connecting an optically trackable body to the movable object, the optically trackable body including a plurality of indicators positioned to form a plurality of geometric figures and including at least one obfuscating flange sized and positioned to optically separate a first of the plurality of indicators from a second of the plurality of indicators;
 (b) viewing one of the plurality of geometric figures positioned in a field of view of an optical detector;
 (c) identifying which one of the plurality of geometric figures is positioned in a field of view of the optical detector;
 (d) analyzing the position and orientation of the identified geometric figure in the field of view of the optical detector to thereby determine the position and orientation of the movable object;
 (e) continuously analyzing the position and orientation of the geometric figure to continuously re-determine the position and orientation of the movable object while the geometric figure remains in the field of view of the optical detector; and
 (f) obfuscating the first of the plurality of indicators to prevent the first of the plurality of indicators from becoming optically coincident with the second of the plurality of indicators, thereby replacing the geometric figure positioned in the field of view of the optical detector with another geometric figure.

32. A method of enhancing detection of a trackable body, the method comprising the steps of:
 (a) positioning an obfuscating flange on a trackable body having a plurality of optical indicators to optically separate a first of the plurality of optical indicators from a second of the plurality of optical indicators; and
 (b) inhibiting the first of the plurality of optical indicators from becoming optically coincident with the second of the plurality of optical indicators when viewing the trackable body along a preselected viewing path extending through the first and the second of the plurality of optical indicators by obfuscating the first of the plurality of optical indicators from the second of the plurality of optical detectors with the obfuscating flange.

33. A method for tracking a position and an orientation of a movable object, comprising the steps of:
 connecting an optically trackable body having a plurality of indicators to the movable object, the optically trackable body including a first obfuscating flange sized and positioned to optically separate a first of the plurality of indicators from a second of the plurality of indicators and a second obfuscating flange sized and positioned to optically separate the second of the plurality of indicators from a third of the plurality of indicators;
 obfuscating the first of the plurality of indicators to prevent the first of the plurality of indicators from becoming optically coincident with the second of the plurality of indicators;
 viewing a subset of the plurality of indicators in a field of view of an optical detector;
 identifying which of the plurality of indicators are positioned in the field of view of the optical detector;

analyzing the position of at least three of the plurality of indicators in the field of view of the optical detector to determine the position and orientation of the movable object;

rotating the optically trackable body;

obfuscating the third of the plurality of indicators to prevent the second of the plurality of indicators from becoming optically coincident with the third of the plurality of indicators, thereby replacing the subset of the plurality of indicators in the field of view of the optical detector with a different subset of the plurality of indicators; and analyzing the position of at least three of the plurality of indicators in the field of view of the optical detector responsive to the steps of rotating and obfuscating to determine the position and orientation of the movable object, the steps of rotating and obfuscating being performed with a varying subset of at least three of the plurality of indicators to continuously re-determine the position and orientation of the movable object when the subset of at least three of the plurality of indicators remains in the field of view of the optical detector.

* * * * *